(12) United States Patent
Himori et al.

(10) Patent No.: US 11,613,509 B2
(45) Date of Patent: Mar. 28, 2023

(54) RADICAL POLYMERIZATION CONTROL AGENT AND RADICAL POLYMERIZATION CONTROL METHOD

(71) Applicant: Kawasaki Kasei Chemicals Ltd., Kawasaki (JP)

(72) Inventors: Shunichi Himori, Kawasaki (JP); Keita Iuchi, Kawasaki (JP)

(73) Assignee: Kawasaki Kasei Chemicals Ltd., Kawasaki (JP)

( * ) Notice: Subject to any disclaimer, the term of this patent is extended or adjusted under 35 U.S.C. 154(b) by 455 days.

(21) Appl. No.: 16/623,890

(22) PCT Filed: Jun. 27, 2018

(86) PCT No.: PCT/JP2018/024399
§ 371 (c)(1),
(2) Date: Dec. 18, 2019

(87) PCT Pub. No.: WO2019/009157
PCT Pub. Date: Jan. 10, 2019

(65) Prior Publication Data
US 2021/0122692 A1  Apr. 29, 2021

(30) Foreign Application Priority Data

Jul. 4, 2017 (JP) ............................. JP2017-130842

(51) Int. Cl.
| | | |
|---|---|---|
| *C07C 43/23* | (2006.01) | |
| *C07C 43/20* | (2006.01) | |
| *C07C 50/32* | (2006.01) | |
| *C07C 255/65* | (2006.01) | |
| *C08F 2/40* | (2006.01) | |
| *C08F 2/48* | (2006.01) | |

(52) U.S. Cl.
CPC .............. *C07C 43/23* (2013.01); *C07C 43/20* (2013.01); *C07C 50/32* (2013.01); *C07C 255/65* (2013.01); *C08F 2/40* (2013.01); *C08F 2/48* (2013.01)

(58) Field of Classification Search
CPC ....... C07C 43/20; C07C 43/202; C07C 43/23; C07C 50/32; C07C 255/65; C08F 2/38; C08F 2/40; C08F 2/46; C08F 2/48; C08F 2/50; C08F 20/00; C08F 20/06; C08F 20/08; C08F 20/18
See application file for complete search history.

(56) References Cited

U.S. PATENT DOCUMENTS

| | | | | |
|---|---|---|---|---|
| 6,093,753 | A * | 7/2000 | Takahashi | G03F 7/038 522/170 |
| 8,926,084 | B2 * | 1/2015 | Hiraoka | B41J 2/17523 347/100 |
| 11,015,007 | B2 * | 5/2021 | Onishi | C08F 220/10 |

FOREIGN PATENT DOCUMENTS

| | | |
|---|---|---|
| JP | 56-86123 A | 7/1981 |
| JP | 63-235390 A | 9/1988 |
| JP | 9-316022 A | 12/1997 |
| JP | 2000-344688 A | 12/2000 |
| JP | 2003-89706 A | 3/2003 |
| JP | 2005-336082 A | 12/2005 |
| JP | 2012-111741 A | 6/2012 |
| JP | 2013144786 A * | 7/2013 |
| JP | 2014-91814 A | 5/2014 |
| JP | 2015-164995 A | 9/2015 |
| JP | 2015-183139 A | 10/2015 |
| JP | 2015-209374 A | 11/2015 |
| JP | 2016-56283 A | 4/2016 |

OTHER PUBLICATIONS

International Search Report dated Sep. 25, 2018 in PCT/JP2018/024399 filed on Jun. 27, 2017, 2 pages.
Chinese Office Action dated Apr. 8, 2022, in Chinese Patent Application No. 201880043965.5 (with English Translation).
"Polymer Materials", Zhou Shanshan et al., Printing Industry Press, 1st Edition, Jun. 1993, p. 130.

(Continued)

*Primary Examiner* — Sanza L. McClendon
(74) *Attorney, Agent, or Firm* — Oblon, McClelland, Maier & Neustadt, L.L.P.

(57) ABSTRACT

A conventional polymerization inhibitor is for example an agent to scavenge radicals generated during storage of a radical polymerizable compound and used to stably handle the radical polymerizable compound, but is unnecessary when the radical polymerizable compound is to be subjected to radical polymerization reaction, and is preferably removed at the time of the radical polymerization reaction. The object of the present invention is to obviate inconvenience of removing the polymerization inhibitor at the time of radical polymerization.

The radical polymerization control agent contained in a radical polymerizable composition of the present invention functions as a radical polymerization inhibitor for example stored in a dark place, but loses its radical polymerization inhibiting effect when polymerization is initiated while being irradiated with light at a certain specific wavelength at the time of polymerization. Thus, radical polymerization of the radical polymerizable compound is easily initiated without increasing the amount of a radical polymerization initiator. That is, the radical polymerization control agent of the present invention is a radical polymerization control agent which is a corn pound having an effect to inhibit radical polymerization of a radical polymerizable compound and which loses the radical polymerization inhibiting effect under irradiation with light rays containing light within a wavelength range of from 300 nm to 500 nm.

10 Claims, No Drawings

(56) References Cited

OTHER PUBLICATIONS

"Polymer Materials", Jia Hongbing et al., Nanjing University Press, 1st Edition, Nov. 2009, p. 112.
"Coating Technology Part II", Coating Technology Editorial Board, Chemical Industry Press, 3rd edition, Dec. 1997, p. 637.

* cited by examiner

US 11,613,509 B2

RADICAL POLYMERIZATION CONTROL AGENT AND RADICAL POLYMERIZATION CONTROL METHOD

TECHNICAL FIELD

The present invention relates to a radical polymerization control agent for a radical polymerizable compound and a radical polymerization control method. Particularly, it relates to a radical polymerization control agent and a radical polymerization control method, which can control radical polymerization of a radical polymerizable compound in a light state and in a dark state.

BACKGROUND ART

The radical polymerization control agent of the present invention is a totally new type of a polymerization control agent which has a radical polymerization inhibiting effect in a state not irradiated with light, but loses the radical polymerization inhibiting effect when irradiated with light at a certain specific wavelength, and a radical polymerization control method using the radical control agent.

Usually, a radical polymerizable compound contains a radical polymerization inhibitor as a storage stabilizer. For example, e.g. an aromatic vinyl compound contains, in order to prevent the monomer from being polymerized e.g. by light, heat or air during storage, a polymerization inhibitor such as a catechol compound such as p-tert-butylcatechol or p-methylcatechol; a hydroquinone compound such as hydroquinone or methoxy hydroquinone; an azine ring compound such as pyrazine, parathiazine, 1,3,5-triazine or phenothiazine; a hydrazine compound such as 1,2-diphenylhydrazine or diphenylpicrylhydrazine; or a phenol compound such as nitrophenol or bisphenol A. However, when polymerization reaction is carried out using such an aromatic vinyl compound or the like, the radical polymerization inhibitor acts as a radical polymerization suppressing agent and delays the polymerization reaction. Accordingly, it is common that the polymerization inhibitor contained is removed e.g. by distillation, adsorption or washing and then reaction is carried out. Further, in a case where the polymerization inhibitor is not removed, it is necessary to increase the amount of a radical polymerization initiator so that its effect exceeds the radical polymerization inhibiting effect of the radical polymerization inhibitor.

For example, styrene contains, to prevent polymerization reaction during storage, a radical polymerization inhibitor such as a catechol compound or a hydroquinone compound in an amount at a level of from 1 to several hundreds ppm. When styrene containing such a radical polymerization inhibitor is homopolymerized or copolymerized to obtain a polymer, the radical polymerization inhibitor reacts with a polymerization catalyst or a polymerization initiator to impair formation of the desired polymer. Accordingly, the polymerization inhibitor in styrene is removed, and purified styrene is polymerized (for example, Patent Documents 1 and 2). It takes time and cost to remove the radical polymerization inhibitor.

Accordingly, a radical polymerization inhibitor which has an ability to scavenge radicals generated in the radical polymerizable compound during storage and which becomes inactive when the radical polymerizable compound is to be radical-polymerized, and such a radical polymerization method, have been desired.

In addition to the above-described radical polymerization inhibitors, a radical polymerization inhibitor of a naphthalene type or a naphthoquinone type has also been known. For example, as a polymerization inhibitor for an aromatic vinyl compound, an alkylated naphthoquinone compound (for example, Patent Document 3) and 2-hydroxy-1,4-naphthoquinone (for example, Patent Document 4) have been known. Further, as a polymerization inhibitor for vinyl acetate, 1,4 naphthoquinone has been known (for example, Patent Document 5), and as a polymerization inhibitor for (meth)acrylic acid and its ester, 1,2-naphthoquinone has been known (for example, Patent Document 6). Further, as a radical polymerization inhibitor for (meth)acrylic acid, a (meth)acrylic acid ester, styrene and the like, an alkoxynaphthol has been known (Patent Document 7).

However, such a polymerization inhibitor is merely a radical polymerization inhibitor used to scavenge generated radicals, is an additive unnecessary in the radical polymerization reaction, and is supposed to be preferably removed at the time of the radical polymerization reaction.

PRIOR ART DOCUMENTS

Patent Documents

Patent Document 1: JP-A-2000-344688
Patent Document 2: JP-A-2015-209374
Patent Document 3: JP-A-S63-235390
Patent Document 4: JP-A-S56-86123
Patent Document 5: JP-A-2003-89706
Patent Document 6: JP-A-H09-316022
Patent Document 7: JP-A-2005-336082

DISCLOSURE OF INVENTION

Technical Problem

The object of the present invention is to provide a radical polymerization control agent which has a role to inhibit unintended polymerization by scavenging generated radicals to improve the stability of the radical polymerizability at the time of storage of a radical polymerizable compound, and which totally loses the radical polymerization inhibiting performance when the radical polymerizable compound is to be polymerized, and to provide a radical polymerization control method using the radical polymerization control agent.

Solution to Problem

The radical polymerization control agent of the present invention acts as a radical polymerization inhibitor to scavenge free radicals in a ground state (dark reaction), but becomes in an excited state and loses its radical scavenging ability when irradiated with light at a certain specific wavelength and becomes inactive in radical polymerization reaction. Further, it has a function to rather promote radical polymerization by transferring the energy in the excited state e.g. to a radical polymerization initiator.

That is, the radical polymerization control agent contained in the radical polymerizable composition of the present invention functions, when stored in a dark place for example, as a radical polymerization inhibitor for a polymerizable compound by scavenging radicals generated by heat or decomposition, but loses its radical polymerization inhibiting effect when polymerization is initiated while being irradiated with light at a certain specific wavelength at the time of polymerization (either thermal polymerization or photopolymerization), and can easily initiate radical polymerization of the radical polymerizable compound without increasing the amount of a radical polymerization initiator.

That is, the present invention has the following constructions.

[1] A radical polymerization control agent represented by the following formula (1), which is a compound having an effect to inhibit radical polymerization of a radical polymerizable compound and which loses the radical polymerization inhibiting effect under irradiation with light rays containing light within a wavelength range of from 300 nm to 500 nm:

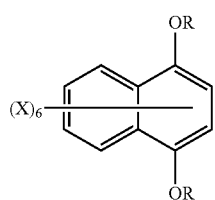

(1)

wherein R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, X is each independently a hydrogen atom, a $C_{1-15}$ alkyl group or a $C_{6-12}$ aryl group, provided that a pair of adjacent Xs may be mutually bonded to form a saturated or unsaturated 6-membered ring, and the 6-membered ring formed by the pair of adjacent Xs may further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom.

[2] A radical polymerization control agent represented by the following formula (2), which is a compound having an effect to inhibit radical polymerization of a radical polymerizable compound and which loses the radical polymerization inhibiting effect under irradiation with light rays containing light within a wavelength range of from 300 nm to 500 nm:

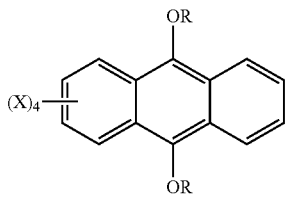

(2)

wherein R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, and X is each independently a hydrogen atom, a $C_{1-15}$ alkyl group or a $C_{6-12}$ aryl group.

[3] A radical polymerization control agent represented by the following formula (3), which is a compound having an effect to inhibit radical polymerization of a radical polymerizable compound and which loses the radical polymerization inhibiting effect under irradiation with light rays containing light within a wavelength range of from 300 nm to 500 nm:

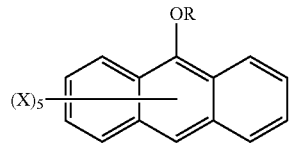

(3)

wherein R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, and X is each independently a hydrogen atom, a $C_{1-15}$ alkyl group or a $C_{6-12}$ aryl group.

[4] A radical polymerization control agent represented by the following formula (4), which is a compound having an effect to inhibit radical polymerization of a radical polymerizable compound and which loses the radical polymerization inhibiting effect under irradiation with light rays containing light within a wavelength range of from 300 nm to 500 nm:

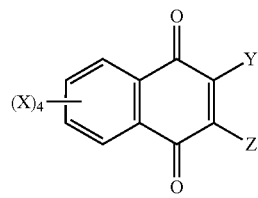

(4)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, Y and Z are each independently a hydrogen atom, a hydroxy group, a $C_{1-15}$ alkyl group, a $C_{1-15}$ alkoxy group, an amino group or a halogen atom, provided that Y and Z may be mutually bonded to form a saturated or unsaturated 6-membered ring, and the 6-membered ring formed by Y and Z may further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom.

[5] The radical polymerization control agent according to [4], wherein in the formula (4), X is a hydrogen atom, and Y and Z are a hydrogen atom.

[6] The radical polymerization control agent according to [4], wherein in the formula (4), X is a hydrogen atom, Y is a hydroxy group, a $C_{1-15}$ alkyl group, a $C_{1-15}$ alkoxy group, an amino group or a halogen atom, and Z is a hydrogen atom.

[7] The radical polymerization control agent according to [4], wherein in the formula (4), X is a hydrogen atom, Y is a hydroxy group or a methyl group, and Z is a hydrogen atom.

[8] The radical polymerization control agent according to [4], wherein in the formula (4), X is a hydrogen atom, Y is a chlorine atom, and Z is a chlorine atom or an amino group.

[9] A radical polymerization control agent represented by the following formula (5) or (6), which is a compound having an effect to inhibit radical polymerization of a radical polymerizable compound and which loses the radical polymerization inhibiting effect under irradiation with light rays containing light within a wavelength range of from 300 nm to 500 nm:

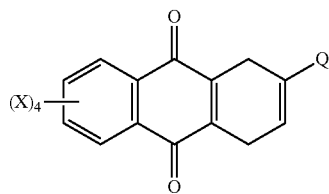

(5)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, and Q is a hydrogen atom, a $C_{1-15}$ alkyl group or a halogen atom;

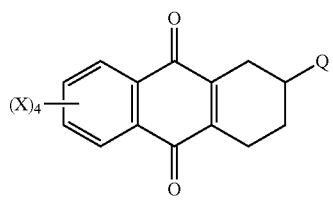

(6)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, and Q is a hydrogen atom, a $C_{1-15}$ alkyl group or a halogen atom.

[10] A radical polymerizable composition, comprising the radical polymerization control agent as defined in any one of [1] to [9], and a radical polymerizable compound.

[11] The radical polymerizable composition according to [10], wherein the radical polymerizable compound is (meth)acrylic acid, a (meth)acrylic acid ester or styrene or an oligomer thereof.

[12] The radical polymerizable composition as defined in [10] or [11], which further contains a radical polymerization initiator.

[13] The radical polymerizable composition according to [12], wherein the radical polymerization initiator is a thermal radical polymerization initiator.

[14] The radical polymerizable composition according to [12], wherein the radical polymerization initiator is a photoradical polymerization initiator.

[15] A radical polymerization control method, which comprises applying a heat energy to the radical polymerizable composition as defined in [13] under irradiation with light rays containing light within a wavelength range of from 300 nm to 500 nm to initiate radical polymerization.

[16] A radical polymerization control method, which comprises applying a heat energy to a coating film formed by applying the radical polymerizable composition as defined in [13] to a substrate, under irradiation with light within a wavelength range of from 300 nm to 500 nm in a state where a part of the coating film is shielded, to conduct radical polymerization, so that the polymerization proceeds only in a portion irradiated with the light.

[17] A radical polymerization control method, which comprises applying a heat energy to the radical polymerizable composition as defined in [13] to conduct radical polymerization, wherein a specific region is irradiated with light rays containing light within a wavelength range of from 300 nm to 500 nm so that the radical polymerization proceeds only in the specific region.

[18] A radical polymerization control method, which comprises applying a light energy to initiate polymerization to the radical polymerizable composition as defined in [14] under irradiation with light rays containing light within a wavelength range of from 300 nm to 500 nm to initiate radical polymerization.

[19] A radical polymerization control method, which comprises irradiating a coating film formed by applying the radical polymerizable composition as defined in [14] to a substrate in a state where a part thereof is shielded, with light within a wavelength range of from 300 nm to 500 nm and simultaneously applying a light energy to initiate polymerization to the coating film thereby to conduct radical polymerization so that the polymerization proceeds only in a portion irradiated with the light within a wavelength range of from 300 nm to 500 nm.

[20] A radical polymerization control method, which comprises irradiating the radical polymerizable composition as defined in [14] with a light energy to initiate polymerization to conduct radical polymerization, wherein a specific region is irradiated with light rays containing light within a wavelength range of from 300 nm to 500 nm so that the radical polymerization proceeds only in the specific region.

Advantageous Effects of Invention

In the radical polymerizable composition containing the radical polymerization control agent of the present invention, when stored in a dark place for example, the radical polymerization control agent acts as a radical polymerization inhibitor, and when the radical polymerizable composition is to be polymerized, the radical polymerization control agent loses its radical polymerization inhibiting effect when polymerization is initiated while being irradiated with light at a certain specific wavelength, and can easily initiate radical polymerization without increasing the amount of a radical polymerization initiator. That is, the radical polymerization control agent of the present invention initiates radical polymerization of a radical polymerizable compound under irradiation with light at a certain specific wavelength (in a light place) and inhibits radical polymerization of the radical polymerizable compound not under irradiation with light at a certain specific wavelength (in a dark place). That is, the radical polymerization control agent of the present invention can control initiation of the radical polymerization of a radical polymerizable compound by lightness/darkness.

DESCRIPTION OF EMBODIMENTS

[Radical Polymerization Control Agent]

The radical polymerization control agent of the present invention is a compound represented by any of the following formulae (1) to (6).

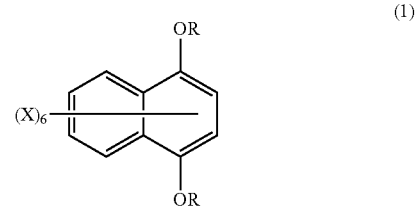

(1)

wherein R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, X is each independently a hydrogen atom, a $C_{1-15}$ alkyl group or a $C_{6-12}$ aryl group, provided that a pair of adjacent Xs may be mutually bonded to form a saturated or unsaturated 6-membered ring, and the 6-membered ring formed by the pair of adjacent Xs may further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom.

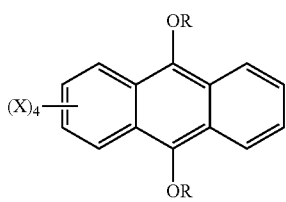

(2)

wherein R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, and X is each independently a hydrogen atom, a $C_{1-15}$ alkyl group or a $C_{6-12}$ aryl group.

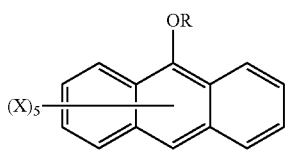

(3)

wherein R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, and X is each independently a hydrogen atom, a $C_{1-15}$ alkyl group or a $C_{6-12}$ aryl group.

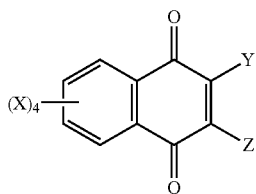

(4)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, Y and Z are each independently a hydrogen atom, a hydroxy group, a $C_{1-15}$ alkyl group, a $C_{1-15}$ alkoxy group, an amino group or a halogen atom, provided that Y and Z may be mutually bonded to form a saturated or unsaturated 6-membered ring, and the 6-membered ring formed by Y and Z may further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom.

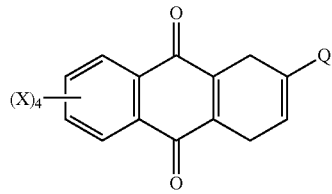

(5)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, and Q is a hydrogen atom, a $C_{1-15}$ alkyl group or a halogen atom;

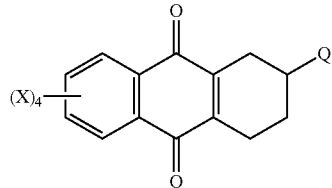

(6)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, and Q is a hydrogen atom, a $C_{1-15}$ alkyl group or a halogen atom.

In the formulae (1) to (3), the alkyl group represented by R may, for example, be a methyl group, an ethyl group, a n-propyl group, an i-propyl group, a n-butyl group, an i-butyl group, a tert-butyl group, a n-pentyl group, a n-hexyl group, a 2-ethylhexyl group, a n-decyl group or a n-dodecyl group, the aryl group may, for example, be a phenyl group, a p-tolyl group, an o-tolyl group or a naphthyl group, the aralkyl group may, for example, be a benzyl group, a phenethyl group, a phenylpropyl group, a naphthylmethyl group or a naphthylethyl group, and the alkoxyalkyl group may, for example, be a 2-methoxyethyl group, a 2-ethoxyethyl group or a 2-methoxyethoxyethyl group. The glycidyl group may, for example, be a glycidyl group or a 2-methylglycidyl group. The hydroxyalkyl group may, for example, be a hydroxymethyl group, a 2-hydroxyethyl group, a 2-hydroxypropyl group, a 3-hydroxypropyl group, a 2-hydroxybutyl group or a 3-hydroxybutyl group. The aryloxyalkyl group may, for example, be a phenoxyethyl group or a tolyloxyethyl group.

In the formulae (1) to (6), the alkyl group represented by X may, for example, be a methyl group, an ethyl group, a n-propyl group, an i-propyl group, a n-butyl group, an i-butyl group, an amyl group, a 2-ethylhexyl group, a 4-methylpentyl group or a 4-methyl-3-pentenyl group, and the aryl group may, for example, be a phenyl group, a p-tolyl group, an o-tolyl group or a naphthyl group. Further, in the formulae (3) to (6), the aralkyl group represented by X may, for example, be a benzyl group, a phenethyl group, a phenylpropyl group, a naphthylmethyl group or a naphthylethyl group, and the alkoxy group may, for example, be a methoxy group, an ethoxy group, a n-propoxy group or an i-propoxy group. The glycidyl group may, for example, be a glycidyl group or a 2-methylglycidyl group. The aryloxy group may, for example, be a phenoxy group or a tolyloxy group. The halogen atom may, for example, be fluorine, chlorine, bromine or iodine.

In the formula (4), the alkyl group represented by each of Y and Z may, for example, be a methyl group, an ethyl group, a n-propyl group, an i-propyl group, a n-butyl group, an i-butyl group, a pentyl group, a 2-ethylhexyl group, a 4-methylpentyl group or a 4-methyl-3-pentenyl group, the alkoxy group may, for example, be a methoxy group, an ethoxy group, a n-propoxy group or an i-propoxy group, and the halogen atom may be fluorine, chlorine, bromine or iodine.

In the formula (4), an example in which Y and Z are mutually bonded is a compound represented by the formula (6), in which Y and Z are a $CH_2CH_2$ group, and Y and Z are bonded by a single bond, or a compound represented by the formula (5) in which Y and Z are a $CH_2CH$ group, and Y and Z are bonded by a double bond. The 6-membered ring formed by Y and Z may further be substituted by an alkyl group, an aryl group, an aralkyl group, a hydroxy group, an alkoxy group, an aryloxy group or a halogen atom.

In the formulae (5) and (6), the alkyl group represented by Q may, for example, be a methyl group, an ethyl group, a n-propyl group, an i-propyl group, a n-butyl group, an i-butyl group, a tert-butyl group, a n-pentyl group, a n-hexyl group, a 2-ethylhexyl group, a n-decyl group or a n-dodecyl group, and the halogen atom may be fluorine, chlorine, bromine or iodine.

Now, specific examples of the radical polymerization control agent of the present invention are shown below.

First, specific examples of the compound represented by the following formula (1) will be described.

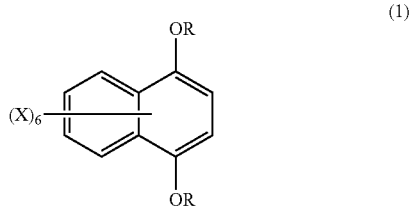

(1)

wherein R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, X is each independently a hydrogen atom, a $C_{1-15}$ alkyl group or a $C_{6-12}$ aryl group, provided that a pair of adjacent Xs may be mutually bonded to form a saturated or unsaturated 6-membered ring, and the 6-membered ring formed by the pair of adjacent Xs may further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom.

As the compound represented by the formula (1), the following compounds may be mentioned. For example, 1,4-dihydroxynaphthalene, 4-methoxy-1-naphthol, 4-ethoxy-1-naphthol, 4-(n-propoxy)-1-naphthol, 4-(n-butoxy)-1-naphthol, 4-(n-pentyloxy)-1-naphthol, 4-(n-hexyloxy)-1-naphthol, 4-(n-heptyloxy)-1-naphthol, 4-(n-octyloxy)-1-naphthol, 4-(2-ethylhexyloxy)-1-naphthol, 4-(n-nonyloxy)-1-naphthol, 4-benzyloxy-1-naphthol, 4-phenethyloxy-1-naphthol, 4-glycidyloxy-1-naphthol, 4-(2-methylglycidyloxy)-1-naphthol, 1,4-dimethoxynaphthalene, 1,4-diethoxynaphthalene, 1,4-di-n-propoxynaphthalene, 1,4-diisopropoxynaphthalene, 1,4-di-n-butoxynaphthalene, 1,4-dihexyloxynaphthalene, 1,4-bis(2-ethylhexyloxy)naphthalene, 1,4-didodecyloxynaphthalene, 1,4-diphenethyloxynaphthalene, 1,4-bis(2-methoxyethoxy)naphthalene, 1,4-bis(2-phenoxyethoxy)naphthalene, 1,4-diglycidyloxynaphthalene, 1,4-bis(2-hydroxyethoxy)naphthalene, 1,4-bis(2-hydroxypropoxy)naphthalene, 1-methoxy-4-ethoxynaphthalene and 1-methoxy-4-butoxynaphthalene may be mentioned.

Further, 2-methyl-1,4-dimethoxynaphthalene, 2-methyl-1,4-diethoxynaphthalene, 2-methyl-1,4-di-n-propoxynaphthalene, 2-methyl-1,4-diisopropoxynaphthalene, 2-methyl-1,4-di-n-butoxynaphthalene, 2-methyl-1,4-dihexyloxynaphthalene, 2-methyl-1,4-bis(2-ethylhexyloxy)naphthalene, 2-methyl-1,4-didodecyloxynaphthalene, 2-methyl-1,4-diphenethyloxynaphthalene, 2-methyl-1,4-bis(2-methoxyethoxy)naphthalene, 2-methyl-1,4-bis(2-phenoxyethoxy)naphthalene, 2-methyl-1,4-diglycidyloxynaphthalene, 2-methyl-1,4-bis(2-hydroxyethoxy)naphthalene, 2-methyl-1,4-bis(2-hydroxypropoxy)naphthalene, 2-ethyl-1,4-diethoxynaphthalene, 6-methyl-1,4-dimethoxynaphthalene, 6-methyl-1,4-diethoxynaphthalene, 6-methyl-1,4-di-n-propoxynaphthalene, 6-methyl-1,4-diisopropoxynaphthalene, 6-methyl-1,4-di-n-butoxynaphthalene, 6-methyl-1,4-dihexyloxynaphthalene, 6-methyl-1,4-bis(2-ethylhexyloxy)naphthalene, 6-methyl-1,4-didodecyloxynaphthalene, 6-methyl-1,4-diphenethyloxynaphthalene, 6-methyl-1,4-bis(2-methoxyethoxy)naphthalene, 6-methyl-1,4-bis(2-phenoxyethoxy)naphthalene, 6-methyl-1,4-diglycidyloxynaphthalene, 6-methyl-1,4-bis(2-hydroxyethoxy)naphthalene, 6-methyl-1,4-bis(2-hydroxypropoxy)naphthalene, 6-ethyl-1,4-diethoxynaphthalene, 2,3-dimethyl-1,4-dimethoxynaphthalene, 2,3-dimethyl-1,4-diethoxynaphthalene, 2,3-dimethyl-1,4-di-n-propoxynaphthalene, 2,3-dimethyl-1,4-diisopropoxynaphthalene, 2,3-dimethyl-1,4-di-n-butoxynaphthalene, 2,3-dimethyl-1,4-dihexyloxynaphthalene, 2,3-dimethyl-1,4-bis(2-ethylhexyloxy)naphthalene, 2,3-dimethyl-1,4-didodecyloxynaphthalene, 2,3-dimethyl-1,4-diphenethyloxynaphthalene, 2,3-dimethyl-1,4-bis(2-methoxyethoxy)naphthalene, 2,3-dimethyl-1,4-bis(2-phenoxyethoxy)naphthalene, 2,3-dimethyl-1,4-diglycidyloxynaphthalene, 2,3-dimethyl-1,4-bis(2-hydroxyethoxy)naphthalene, 2,3-dimethyl-1,4-bis(2-hydroxypropoxy)naphthalene may, for example, be mentioned.

As specific examples of the compound of the formula (1) wherein R is a $C_{2-13}$ acyl group, for example, the following compounds may be mentioned. That is, as examples in which X is a hydrogen atom, 1,4-bis(acetyloxy)naphthalene, 1,4-bis(propionyloxy)naphthalene, 1,4-bis(n-butyryloxy)naphthalene, 1,4-bis(i-butyryloxy)naphthalene, 1,4-bis(n-pentanoyloxy)naphthalene, 1,4-bis(n-hexanoyloxy)naphthalene, 1,4-bis(n-heptanoyloxy)naphthalene, 1,4-bis(n-octanoyloxy)naphthalene, 1,4-bis(2-ethylhexanoyloxy)naphthalene, 1,4-bis(n-nonanoyloxy)naphthalene, 1,4-bis(n-decanoyloxy)naphthalene, 1,4-bis(n-undecanoyloxy)naphthalene and 1,4-bis(n-dodecanoyloxy)naphthalene may, for example, be mentioned.

Further, as examples in which X is an alkyl group, 2-methyl-1,4-bis(acetyloxy)naphthalene, 2-methyl-1,4-bis(propionyloxy)naphthalene, 2-methyl-1,4-bis(n-butyryloxy)naphthalene, 2-methyl-1,4-bis(i-butyryloxy)naphthalene, 2-methyl-1,4-bis(n-pentanoyloxy)naphthalene, 2-methyl-1, 4-bis(n-hexanoyloxy)naphthalene, 2-methyl-1,4-bis(n-heptanoyloxy)naphthalene, 2-methyl-1,4-bis(n-octanoyloxy) naphthalene, 2-methyl-1,4-bis(2-ethylhexanoyloxy) naphthalene, 2-methyl-1,4-bis(n-nonanoyloxy)naphthalene, 2-methyl-1,4-bis(n-decanoyloxy)naphthalene, 2-methyl-1, 4-bis(n-undecanoyloxy)naphthalene, 2-methyl-1,4-bis(n-dodecanoyloxy)naphthalene, 2-ethyl-1,4-bis(acetyloxy) naphthalene, 2-ethyl-1,4-bis(propionyloxy)naphthalene, 2-ethyl-1,4-bis(n-butyryloxy)naphthalene, 2-ethyl-1,4-bis(i-butyryloxy)naphthalene, 2-ethyl-1,4-bis(n-pentanoyloxy) naphthalene, 2-ethyl-1,4-bis(n-hexanoyloxy)naphthalene, 2-ethyl-1,4-bis(n-heptanoyloxy)naphthalene, 2-ethyl-1,4-bis(n-octanoyloxy)naphthalene, 2-ethyl-1,4-bis(2-ethylhexanoyloxy)naphthalene, 2-ethyl-1,4-bis(n-nonanoyloxy) naphthalene, 2-ethyl-1,4-bis(n-decanoyloxy)naphthalene, 2-ethyl-1,4-bis(n-undecanoyloxy)naphthalene and 2-ethyl-1,4-bis(n-dodecanoyloxy)naphthalene may, for example, be mentioned.

As specific examples of the compound of the formula (1) wherein R is a $C_{2-13}$ substituted carbonyl group, as examples in which X is a hydrogen atom, 1,4-bis(methoxycarbonyloxy)naphthalene, 1,4-bis(ethoxycarbonyloxy)naphthalene, 1,4-bis(n-propoxycarbonyloxy)naphthalene, 1,4-bis(i-propoxycarbonyloxy)naphthalene, 1,4-bis(n-butoxycarbonyloxy)naphthalene, 1,4-bis(n-pentoxycarbonyloxy)naphthalene, 1,4-bis(n-hexyloxycarbonyloxy)naphthalene, 1,4-bis(n-heptyloxycarbonyloxy)naphthalene, 1,4-bis(n-octyloxycarbonyloxy)naphthalene, 1,4-bis(2-ethylhexyloxycarbonyloxy)naphthalene, 1,4-bis(n-nonyloxycarbonyloxy)naphthalene, 1,4-bis(n-decyloxycarbonyloxy)naphthalene, 1,4-bis(n-undecyloxycarbonyloxy)naphthalene and 1,4-bis(n-dodecyloxycarbonyloxy)naphthalene may, for example, be mentioned.

As examples in which X is an alkyl group, 2-methyl-1, 4-bis(methoxycarbonyloxy)naphthalene, 2-methyl-1,4-bis (ethoxycarbonyloxy)naphthalene, 2-methyl-1,4-bis(n-propoxycarbonyloxy)naphthalene, 2-methyl-1,4-bis(i-propoxycarbonyloxy)naphthalene, 2-methyl-1,4-bis(n-butoxycarbonyloxy)naphthalene, 2-methyl-1,4-bis(n-pentoxycarbonyloxy)naphthalene, 2-methyl-1,4-bis(n-hexyloxycarbonyloxy)naphthalene, 2-methyl-1,4-bis(n-heptyloxycarbonyloxy)naphthalene, 2-methyl-1,4-bis(n-octyloxycarbonyloxy)naphthalene, 2-methyl-1,4-bis(2-ethylhexyloxycarbonyloxy)naphthalene, 2-methyl-1,4-bis (n-nonyloxycarbonyloxy)naphthalene, 2-methyl-1,4-bis(n-decyloxycarbonyloxy)naphthalene, 2-methyl-1,4-bis(n-undecyloxycarbonyloxy)naphthalene, 2-methyl-1,4-bis(n-dodecyloxycarbonyloxy)naphthalene, 2-ethyl-1,4-bis (methoxycarbonyloxy)naphthalene, 2-ethyl-1,4-bis (ethoxycarbonyloxy)naphthalene, 2-ethyl-1,4-bis(n-propoxycarbonyloxy)naphthalene, 2-ethyl-1,4-bis(i-propoxycarbonyloxy)naphthalene, 2-ethyl-1,4-bis(n-butoxycarbonyloxy)naphthalene, 2-ethyl-1,4-bis(n-pentoxycarbonyloxy)naphthalene, 2-ethyl-1,4-bis(n-hexyloxycarbonyloxy)naphthalene, 2-ethyl-1,4-bis(n-heptyloxycarbonyloxy)naphthalene, 2-ethyl-1,4-bis(n-octyloxycarbonyloxy)naphthalene, 2-ethyl-1,4-bis(2-ethylhexyloxycarbonyloxy)naphthalene, 2-ethyl-1,4-bis(n-nonyloxycarbonyloxy)naphthalene, 2-ethyl-1,4-bis(n-decyloxycarbonyloxy)naphthalene, 2-ethyl-1,4-bis(n-undecyloxycarbonyloxy)naphthalene and 2-ethyl-1,4-bis(n-dodecyloxycarbonyloxy)naphthalene may, for example, be mentioned.

Further, as specific examples of the compound of the formula (1) wherein a pair of adjacent Rs are mutually bonded to form a saturated 6-membered ring, 9,10-dimethoxy-1,2,3,4-tetrahydroanthracene, 9,10-diethoxy-1,2,3,4-tetrahydroanthracene, 9,10-di-n-propoxy-1,2,3,4-tetrahydroanthracene, 9,10-diisopropoxy-1,2,3,4-tetrahydroanthracene, 9,10-di-n-butoxy-1,2,3,4-tetrahydroanthracene, 9,10-bis(2-ethylhexyloxy)-1,2,3,4-tetrahydroanthracene, 9,10-didodecyloxy-1,2,3,4-tetrahydroanthracene, 9,10-diphenethyloxy-1,2,3,4-tetrahydroanthracene, 9,10-bis(2-methoxyethoxy)-1,2,3,4-tetrahydroanthracene, 9,10-bis(2-phenoxyethoxy)-1,2,3,4-tetrahydroanthracene, 9,10-bis(2-hydroxyethoxy)-1,2,3,4-tetrahydroanthracene, 9-methoxy-10-ethoxy-1,2,3,4-tetrahydroanthracene, 9-methoxy-10-butoxy-1,2,3,4-tetrahydroanthracene, 2-methyl-9,10-diethoxy-1,2,3,4-tetrahydroanthracene and 2-ethyl-9,10-diethoxy-1,2,3,4-tetrahydroanthracene may, for example, be mentioned.

Further, as specific examples of the compound of the formula (1) in which a pair of adjacent Rs are mutually bonded to form an unsaturated 6-membered ring which is not aromatic, 9,10-dimethoxy-1,4-dihydroanthracene, 9,10-diethoxy-1,4-dihydroanthracene, 9,10-di-n-propoxy-1,4-dihydroanthracene, 9,10-diisopropoxy-1,4-dihydroanthracene, 9,10-di-n-butoxy-1,4-dihydroanthracene, 9,10-bis(2-ethylhexyloxy)-1,4-dihydroanthracene, 9,10-didodecyloxy-1,4-dihydroanthracene, 9,10-diphenethyloxy-1,4-dihydroanthracene, 9,10-bis(2-methoxyethoxy)-1,4-dihydroanthracene, 9,10-bis(2-phenoxyethoxy)-1,4-dihydroanthracene, 9,10-bis(2-hydroxyethoxy)-1,4-dihydroanthracene, 9-methoxy-10-ethoxy-1,4-dihydroanthracene, 9-methoxy-10-butoxy-1,4-dihydroanthracene, 2-methyl-9,10-diethoxy-1,4-dihydroanthracene and 2-ethyl-9,10-diethoxy-1,4-dihydroanthracene may, for example, be mentioned.

Now, specific examples of the compound represented by the following formula (2) will be described.

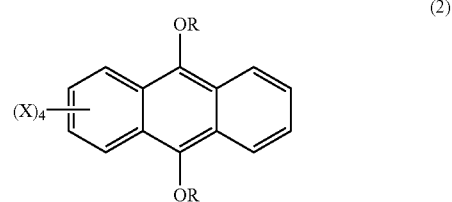

(2)

wherein R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, and X is each independently a hydrogen atom, a $C_{1-15}$ alkyl group or a $C_{6-12}$ aryl group.

As specific examples of the compound of the formula (2) wherein R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group or a $C_{7-14}$ aryloxyalkyl group, and X is a hydrogen atom, 9,10-dimethoxyanthracene, 9,10-diethoxyanthracene, 9,10-di-n-propoxyanthracene, 9,10-diisopropoxyanthracene, 9,10-di-n-butoxyanthracene, 9,10-bis(2-ethylhexyloxy)anthracene, 9,10-didodecyloxyanthracene, 9,10-diphenethyloxyanthracene, 9,10-bis(2-methoxyethoxy)anthracene, 9,10-bis(2-phenoxyethoxy)anthracene, 9,10-bis(2-hydroxyethoxy)anthracene, 9,10-diglycidyloxyanthracene, 9-methoxy-10-ethoxyanthracene and 9-methoxy-10-butoxyanthracene may, for example, be mentioned.

Further, as examples in which X is an alkyl group, 2-methyl-9,10-dimethoxyanthracene, 2-methyl-9,10-diethoxyanthracene, 2-methyl-9,10-di-n-propoxyanthracene, 2-methyl-9,10-diisopropoxyanthracene, 2-methyl-9,10-di-n-butoxyanthracene, 2-methyl-9,10-bis(2-ethylhexyloxy) anthracene, 2-methyl-9,10-didodecyloxyanthracene, 2-methyl-9,10-diphenethyloxyanthracene, 2-methyl-9,10-bis(2-methoxyethoxy)anthracene, 2-methyl-9,10-bis(2-phenoxyethoxy)anthracene, 2-methyl-9,10-bis(2-hydroxyethoxy)anthracene, 2-methyl-9,10-diglycidyloxyanthracene, 9-methoxy-10-ethoxyanthracene, 9-m ethoxy-10-butoxyanthracene, 2-methyl-2-methyl-9,10-diethoxyanthracene, 2-ethyl-2-methyl-9,10-diethoxyanthracene, 2-ethyl-9,10-dimethoxyanthracene, 2-ethyl-9,10-diethoxyanthracene, 2-ethyl-9,10-di-n-propoxyanthracene, 2-ethyl-9,10-diisopropoxyanthracene, 2-ethyl-9,10-di-n-butoxyanthracene, 2-ethyl-9,10-bis(2-ethylhexyloxy)anthracene, 2-ethyl-9,10-didodecyloxyanthracene, 2-ethyl-9,10-diphenethyloxyanthracene, 2-ethyl-9,10-bis(2-methoxyethoxy)anthracene, 2-ethyl-9,10-bis(2-phenoxyethoxy)anthracene, 2-ethyl-9, 10-bis(2-hydroxyethoxy)anthracene, 2-ethyl-9,10-diglycidyloxyanthracene, 9-methoxy-10-ethoxyanthracene, 9-methoxy-10-butoxyanthracene, 2-methyl-2-ethyl-9,10-diethoxyanthracene and 2-ethyl-2-ethyl-9,10-diethoxyanthracene may, for example, be mentioned.

As specific examples of the compound of the formula (2) wherein R is a $C_{2-13}$ acyl group, for example, the following compounds may be mentioned. That is, as examples in which X is a hydrogen atom, 9,10-bis(acetyloxy)anthracene, 9,10-bis(propionyloxy)anthracene, 9,10-bis(n-butyryloxy) anthracene, 9,10-bis(i-butyryloxy)anthracene, 9,10-bis(n-pentanoyloxy)anthracene, 9,10-bis(n-hexanoyloxy)anthracene, 9,10-bis(n-heptanoyloxy)anthracene, 9,10-bis(n-octanoyloxy)anthracene, 9,10-bis(2-ethylhexanoyloxy) anthracene, 9,10-bis(n-nonanoyloxy)anthracene, 9,10-bis(n-decanoyloxy)anthracene, 9,10-bis(n-undecanoyloxy) anthracene and 9,10-bis(n-dodecanoyloxy)anthracene may, for example, be mentioned.

Further, as examples in which X is an alkyl group, 2-methyl-9,10-bis(acetyloxy)anthracene, 2-methyl-9,10-bis (propionyloxy)anthracene, 2-methyl-9,10-bis(n-butyryloxy) anthracene, 2-methyl-9,10-bis(i-butyryloxy)anthracene, 2-methyl-9,10-bis(n-pentanoyloxy)anthracene, 2-methyl-9, 10-bis(n-hexanoyloxy)anthracene, 2-methyl-9,10-bis(n-heptanoyloxy)anthracene, 2-methyl-9,10-bis(n-octanoyloxy)anthracene, 2-methyl-9,10-bis(2-ethylhexanoyloxy) anthracene, 2-methyl-9,10-bis(n-nonanoyloxy)anthracene, 2-methyl-9,10-bis(n-decanoyloxy)anthracene, 2-methyl-9, 10-bis(n-undecanoyloxy)anthracene, 2-methyl-9,10-bis(n-dodecanoyloxy)anthracene, 2-ethyl-9,10-bis(acetyloxy)anthracene, 2-ethyl-9,10-bis(propionyloxy)anthracene, 2-ethyl-9,10-bis(n-butyryloxy)anthracene, 2-ethyl-9,10-bis (i-butyryloxy)anthracene, 2-ethyl-9,10-bis(n-pentanoyloxy) anthracene, 2-ethyl-9,10-bis(n-hexanoyloxy)anthracene, 2-ethyl-9,10-bis(n-heptanoyloxy)anthracene, 2-ethyl-9,10-bis(n-octanoyloxy)anthracene, 2-ethyl-9,10-bis(2-ethylhexanoyloxy)anthracene, 2-ethyl-9,10-bis(n-nonanoyloxy) anthracene, 2-ethyl-9,10-bis(n-decanoyloxy)anthracene, 2-ethyl-9,10-bis(n-undecanoyloxy)anthracene and 2-ethyl-9,10-bis(n-dodecanoyloxy)anthracene may, for example, be mentioned.

As specific examples of the compound of the formula (2) wherein R is a $C_{2-13}$ substituted carbonyl group, as examples in which X is a hydrogen atom, 9,10-bis(methoxycarbonyloxy)anthracene, 9,10-bis(ethoxycarbonyloxy)anthracene, 9,10-bis(n-propoxycarbonyloxy)anthracene, 9,10-bis(i-propoxycarbonyloxy)anthracene, 9,10-bis(n-butoxycarbonyloxy)anthracen e, 9,10-bis(n-pentoxycarbonyloxy)anthracene, 9,10-bis(n-hexyloxycarbonyloxy)anthracene, 9,10-bis (n-heptyloxycarbonyloxy)anthracene, 9,10-bis(n-octyloxycarbonyloxy)anthracene, 9,10-bis(2-ethylhexyloxycarbonyloxy)anthracene, 9,10-bis(n-nonyloxycarbonyloxy)anthracene, 9,10-bis(n-decyloxycarbonyloxy)anthracene, 9,10-bis(n-undecyloxycarbonyloxy)anthracene and 9,10-bis(n-dodecyloxycarbonyloxy)anthracene may, for example, be mentioned.

Further, as examples in which X is an alkyl group, 2-methyl-9,10-bis(methoxycarbonyloxy)anthracene, 2-methyl-9,10-bis(ethoxycarbonyloxy)anthracene, 2-methyl-9,10-bis(n-propoxycarbonyloxy)anthracene, 2-methyl-9,10-bis(i-propoxycarbonyloxy)anthracene, 2-methyl-9,10-bis(n-butoxycarbonyloxy)anthracene, 2-methyl-9,10-bis(n-pentoxycarbonyloxy)anthracene, 2-methyl-9,10-bis(n-hexyloxycarbonyloxy)anthracene, 2-methyl-9,10-bis(n-heptyloxycarbonyloxy)anthracene, 2-methyl-9,10-bis(n-octyloxycarbonyloxy)anthracene, 2-methyl-9,10-bis(2-ethylhexyloxycarbonyloxy)anthracene, 2-methyl-9,10-bis(n-nonyloxycarbonyloxy)anthracene, 2-methyl-9,10-bis(n-decyloxycarbonyloxy)anthracene, 2-methyl-9,10-bis(n-undecyloxycarbonyloxy)anthracene, 2-methyl-9,10-bis(n-dodecyloxycarbonyloxy)anthracene, 2-ethyl-9,10-bis(methoxycarbonyloxy)anthracene, 2-ethyl-9,10-bis(ethoxycarbonyloxy)anthracene, 2-ethyl-9,10-bis(n-propoxycarbonyloxy)anthracene, 2-ethyl-9,10-bis(i-propoxycarbonyloxy)anthracene, 2-ethyl-9,10-bis(n-butoxycarbonyloxy)anthracene, 2-ethyl-9,10-bis(n-pentoxycarbonyloxy)anthracene, 2-ethyl-9,10-bis(n-hexyloxycarbonyloxy)anthracene, 2-ethyl-9,10-bis(n-heptyloxycarbonyloxy)anthracene, 2-ethyl-9,10-bis(n-octyloxycarbonyloxy)anthracene, 2-ethyl-9,10-bis(2-ethylhexyloxycarbonyloxy)anthracene, 2-ethyl-9,10-bis(n-nonyloxycarbonyloxy)anthracene, 2-ethyl-9,10-bis(n-decyloxycarbonyloxy)anthracene, 2-ethyl-9,10-bis(n-undecyloxycarbonyloxy)anthracene and 2-ethyl-9,10-bis(n-dodecyloxycarbonyloxy)anthracene may, for example, be mentioned.

Now, specific examples of the compound represented by the following formula (3) will be described.

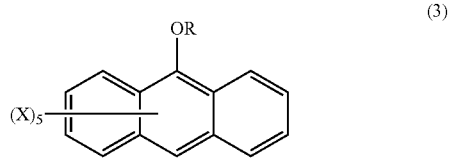

(3)

wherein R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group, and X is each independently a hydrogen atom, a $C_{1-15}$ alkyl group or a $C_{6-12}$ aryl group.

As specific examples of the compound of the formula (3) wherein R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group or a $C_{7-14}$ aryloxyalkyl group, and X is a hydrogen atom, 9-m ethoxyanthracene, 9-ethoxyanthracene, 9-n-propoxyanthracene, 9-isopropoxyanthracene, 9-n-butoxyanthracene, 9-(2-ethylhexyloxy)anthracene, 9-dodecyloxyanthracene, 9-phenethyloxyanthracene, 9-(2-m ethoxyethoxy)anthracene, 9-(2-phenoxyethoxy)anthracene, 9,10-bis(2-hydroxyethoxy)anthracene and 9-glycidyloxyanthracene may, for example, be mentioned.

Further, as examples in which X is an alkyl group, 2-methyl-9-methoxyanthracene, 2-methyl-9-ethoxyanthracene, 2-methyl-9-n-propoxyanthracene, 2-methyl-9-isopropoxyanthracene, 2-methyl-9-n-butoxyanthracene, 2-methyl-9-(2-ethylhexyloxy)anthracene, 2-methyl-9-dodecyloxyanthracene, 2-methyl-9-phenethyloxyanthracene, 2-methyl-9-(2-methoxyethoxy)anthracene, 2-methyl-9-(2-phenoxyethoxy)anthracene, 9,10-bis(2-hydroxyethoxy)anthracene, 2-methyl-9-glycidyloxyanthracene, 2-ethyl-9-methoxyanthracene, 2-ethyl-9-ethoxyanthracene, 2-ethyl-9-n-propoxyanthracene, 2-ethyl-9-isopropoxyanthracene, 2-ethyl-9-n-butoxyanthracene, 2-ethyl-9-(2-ethylhexyloxy)anthracene, 2-ethyl-9-dodecyloxyanthracene, 2-ethyl-9-phenethyloxyanthracene, 2-ethyl-9-(2-methoxyethoxy)anthracene, 2-ethyl-9-(2-phenoxyethoxy)anthracene, 9,10-bis(2-hydroxyethoxy)anthracene and 2-ethyl-9-glycidyloxyanthracene may, for example, be mentioned.

As specific examples of the compound of the formula (3) wherein R is a $C_{2-13}$ acyl group, for example, the following compounds may be mentioned. For example, as examples in which X is a hydrogen atom, 9,10-bis(acetyloxy)anthracene, 9,10-bis(propionyloxy)anthracene, 9,10-bis(n-butyryloxy)anthracene, 9,10-bis(i-butyryloxy)anthracene, 9,10-bis(n-pentanoyloxy)anthracene, 9,10-bis(n-hexanoyloxy)anthracene, 9,10-bis(n-heptanoyloxy)anthracene, 9,10-bis(n-octanoyloxy)anthracene, 9,10-bis(2-ethylhexanoyloxy)anthracene, 9,10-bis(n-nonanoyloxy)anthracene, 9,10-bis(n-decanoyloxy)anthracene, 9,10-bis(n-undecanoyloxy)anthracene and 9,10-bis(n-dodecanoyloxy)anthracene may, for example, be mentioned.

Now, as examples in which X is an alkyl group, 2-methyl-9,10-bis(acetyloxy)anthracene, 2-methyl-9,10-bis(propionyloxy)anthracene, 2-methyl-9,10-bis(n-butyryloxy)anthracene, 2-methyl-9,10-bis(i-butyryloxy)anthracene, 2-methyl-9,10-bis(n-pentanoyloxy)anthracene, 2-methyl-9,10-bis(n-hexanoyloxy)anthracene, 2-methyl-9,10-bis(n-heptanoyloxy)anthracene, 2-methyl-9,10-bis(n-octanoyloxy)anthracene, 2-methyl-9,10-bis(2-ethylhexanoyloxy)anthracene, 2-methyl-9,10-bis(n-nonanoyloxy)anthracene, 2-methyl-9,10-bis(n-decanoyloxy)anthracene, 2-methyl-9,10-bis(n-undecanoyloxy)anthracene, 2-methyl-9,10-bis(n-dodecanoyloxy)anthracene, 2-ethyl-9,10-bis(acetyloxy)anthracene, 2-ethyl-9,10-bis(propionyloxy)anthracene, 2-ethyl-9,10-bis(n-butyryloxy)anthracene, 2-ethyl-9,10-bis(i-butyryloxy)anthracene, 2-ethyl-9,10-bis(n-pentanoyloxy)anthracene, 2-ethyl-9,10-bis(n-hexanoyloxy)anthracene, 2-ethyl-9,10-bis(n-heptanoyloxy)anthracene, 2-ethyl-9,10-bis(n-octanoyloxy)anthracene, 2-ethyl-9,10-bis(2-ethylhexanoyloxy)anthracene, 2-ethyl-9,10-bis(n-nonanoyloxy)anthracene, 2-ethyl-9,10-bis(n-decanoyloxy)anthracene, 2-ethyl-9,10-bis(n-undecanoyloxy)anthracene and 2-ethyl-9,10-bis(n-dodecanoyloxy)anthracene may, for example, be mentioned.

As specific examples of the compound of the formula (3) wherein R is a $C_{2-13}$ substituted carbonyl group, as examples in which X is a hydrogen atom, 9-methoxycarbonyloxyanthracene, 9-ethoxycarbonyloxyanthracene, 9-(n-propoxycarbonyloxy)anthracene, 9-(i-propoxycarbonyloxy)anthracene, 9-(n-butoxycarbonyloxy)anthracene, 9-(n-pentoxycarbonyloxy)anthracene, 9-(n-hexyloxycarbonyloxy)anthracene, 9-(n-heptyloxycarbonyloxy)anthracene, 9-(n-octyloxycarbonyloxy)anthracene, 9-(2-ethylhexyloxycarbonyloxy)anthracene, 9-(n-nonyloxycarbonyloxy)anthracene, 9-(n-decyloxycarbonyloxy)anthracene, 9-(n-undecyloxycarbonyloxy)anthracene and 9-(n-dodecyloxycarbonyloxy)anthracene may, for example, be mentioned.

Further, as examples in which X is an alkyl group, 2-methyl-9-methoxycarbonyloxyanthracene, 2-methyl-9-ethoxycarbonyloxyanthracene, 2-methyl-9-(n-propoxycarbonyloxy)anthracene, 2-methyl-9-(i-propoxycarbonyloxy)anthracene, 2-methyl-9-(n-butoxycarbonyloxy)anthracene, 2-methyl-9-(n-pentoxycarbonyloxy)anthracene, 2-methyl-9-(n-hexyloxycarbonyloxy)anthracene, 2-methyl-9-(n-heptyloxycarbonyloxy)anthracene, 2-methyl-9-(n-octyloxycarbonyloxy)anthracene, 2-methyl-9-(2-ethylhexyloxycarbonyloxy)anthracene, 2-methyl-9-(n-nonyloxycarbonyloxy)anthracene, 2-methyl-9-(n-decyloxycarbonyloxy)anthracene, 2-methyl-9-(n-undecyloxycarbonyloxy)anthracene, 2-methyl-9-(n-dodecyloxycarbonyloxy)anthracene, 2-ethyl-9-methoxycarbonyloxyanthracene, 2-ethyl-9-ethoxycarbonyloxyanthracene, 2-ethyl-9-(n-propoxycarbonyloxy)anthracene, 2-ethyl-9-(i-propoxycarbonyloxy)anthracene, 2-ethyl-9-(n-butoxycarbonyloxy)anthracene, 2-ethyl-9-(n-pentoxycarbonyloxy)anthracene, 2-ethyl-9-(n-hexyloxycarbonyloxy)anthracene, 2-ethyl-9-(n-heptyloxycarbonyloxy)anthracene, 2-ethyl-9-(n-octyloxycarbonyloxy)anthracene, 2-ethyl-9-(2-ethylhexyloxycarbonyloxy)anthracene, 2-ethyl-9-(n-nonyloxycarbonyloxy)anthracene, 2-ethyl-9-(n-decyloxycarbonyloxy)anthracene, 2-ethyl-9-(n-undecyloxycarbonyloxy)anthracene and 2-ethyl-9-(n-dodecyloxycarbonyloxy)anthracene may, for example, be mentioned.

Now, specific examples of the compound represented by the following formula (4) will be described.

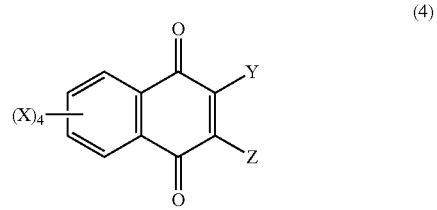

(4)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, Y and Z are each independently a hydrogen atom, a hydroxy group, a $C_{1-15}$ alkyl group, a $C_{1-15}$ alkoxy group, an amino group or a halogen atom, provided that Y and Z may be mutually bonded to form a saturated or unsaturated 6-membered ring, and the 6-membered ring formed by Y and Z may further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom.

As specific examples of the compound represented by the formula (4), first, as a compound wherein Y and Z are a hydrogen atom, the following compounds may be mentioned. For example, 1,4-naphthoquinone, 5-methyl-1,4-naphthoquinone, 6-methyl-1,4-naphthoquinone, 6,7-dimethyl-1,4-naphthoquinone, 5-butyl-1,4-naphthoquinone, 6-butyl-1,4-naphthoquinone, 6,7-dibutyl-1,4-naphthoquinone, 5-pentyl-1,4-naphthoquinone, 6-pentyl-1,4-naphthoquinone, 5-chloro-1,4-naphthoquinone, 6-chloro-1,4-naphthoquinone, 6,7-dichloro-1,4-naphthoquinone, 5-hydroxy-1,4-naphthoquinone, 6-hydroxy-1,4-naphthoquinone, 5,8-dihydroxy-1,4-naphthoquinone, 5,6,8-trihydroxy-1,4-naphthoquinone, 5-methoxy-1,4-naphthoquinone, 6-methoxy-1,4-naphthoquinone and 5,8-dimethoxy-1,4-naphthoquinone may, for example, be mentioned.

Further, as a compound of the formula (4) wherein Y is a hydroxy group, an alkyl group, an alkoxy group, an amino group or a halogen atom, and Z is a hydrogen atom, the following compounds may be mentioned. For example, 2-methyl-1,4-naphthoquinone, 2-ethyl-1,4-naphthoquinone, 2-hydroxy-1,4-naphthoquinone, 2-methoxy-1,4-naphthoquinone, 2-chloro-1,4-naphthoquinone, 2-amino-1,4-naphthoquinone, 2,5-dimethyl-1,4-naphthoquinone, 2,6-dimethyl-1,4-naphthoquinone, 2,6,7-trimethyl-1,4-naphthoquinone, 2-methyl-5-butyl-1,4-naphthoquinone, 2-methyl-6-butyl-1,4-naphthoquinone, 2-methyl-6,7-dibutyl-1,4-naphthoquinone, 2-methyl-5-pentyl-1,4-naphthoquinone, 2-methyl-6-pentyl-1,4-naphthoquinone, 2-methyl-5-chloro-1,4-naphthoquinone, 2-methyl-6-chloro-1,4-naphthoquinone, 2-methyl-6,7-dichloro-1,4-naphthoquinone, 2-methyl-5-hydroxy-1,4-naphthoquinone, 2-methyl-6-hydroxy-1,4-naphthoquinone, 2-methyl-5,8-dihydroxy-1,4-naphthoquinone, 2-methyl-5,6,8-trihydroxy-1,4-naphthoquinone, 2-methyl-5-methoxy-1,4-naphthoquinone, 2-methyl-6-methoxy-1,4-naphthoquinone, 2-methyl-5,8-dimethoxy-1,4-naphthoquinone, 2-hydroxy-5-methyl-1,4-naphthoquinone, 2-ethyl-5-methyl-1,4-naphthoquinone, 2-ethyl-6-methyl-1,4-naphthoquinone, 2-ethyl-6,7-dimethyl-1,4-naphthoquinone, 2-ethyl-5-butyl-1,4-naphthoquinone, 2-ethyl-6-butyl-1,4-naphthoquinone, 2-ethyl-6,7-dibutyl-1,4-naphthoquinone, 2-ethyl-5-pentyl-1,4-naphthoquinone, 2-ethyl-6-pentyl-1,4-naphthoquinone, 2-ethyl-5-chloro-1,4-naphthoquinone, 2-ethyl-6-chloro-1,4-naphthoquinone, 2-ethyl-6,7-dichloro-1,4-naphthoquinone, 2-ethyl-5-hydroxy-1,4-naphthoquinone, 2-ethyl-6-hydroxy-1,4-naphthoquinone, 2-ethyl-5,8-dihydroxy-1,4-naphthoquinone, 2-ethyl-5,6,8-trihydroxy-1,4-naphthoquinone, 2-ethyl-5-methoxy-1,4-naphthoquinone, 2-ethyl-6-methoxy-1,4-naphthoquinone, 2-ethyl-5,8-dimethoxy-1,4-naphthoquinone, 2-hydroxy-6-methyl-1,4-naphthoquinone, 2-hydroxy-6,7-dimethyl-1,4-naphthoquinone, 2-hydroxy-5-butyl-1,4-naphthoquinone, 2-hydroxy-6-butyl-1,4-naphthoquinone, 2-hydroxy-6,7-dibutyl-1,4-naphthoquinone, 2-hydroxy-5-pentyl-1,4-naphthoquinone, 2-hydroxy-6-pentyl-1,4-naphthoquinone, 2-hydroxy-5-chloro-1,4-naphthoquinone, 2-hydroxy-6-chloro-1,4-naphthoquinone, 2-hydroxy-6,7-dichloro-1,4-naphthoquinone, 2,5-dihydroxy-1,4-naphthoquinone, 2,6-dihydroxy-1,4-naphthoquinone, 2,5,8-trihydroxy-1,4-naphthoquinone, 2,5,6,8-tetrahydroxy-1,4-naphthoquinone, 2-hydroxy-5-methoxy-1,4-naphthoquinone, 2-hydroxy-6-methoxy-1,4-naphthoquinone, 2-hydroxy-5,8-dimethoxy-1,4-naphthoquinone, 2-methoxy-5-methyl-1,4-naphthoquinone, 2-methoxy-6-methyl-1,4-naphthoquinone, 2-methoxy-6,7-dimethyl-1,4-naphthoquinone, 2-methoxy-5-butyl-1,4-naphthoquinone, 2-methoxy-6-butyl-1,4-naphthoquinone, 2-methoxy-6,7-dibutyl-1,4-naphthoquinone, 2-methoxy-5-pentyl-1,4-naphthoquinone, 2-methoxy-6-pentyl-1,4-naphthoquinone, 2-methoxy-5-chloro-1,4-naphthoquinone, 2-methoxy-6-chloro-1,4-naphthoquinone, 2-m ethoxy-6,7-dichloro-1,4-naphthoquinone, 2-methoxy-5-hydroxy-1,4-naphthoquinone, 2-methoxy-6-hydroxy-1,4-naphthoquinone, 2-methoxy-5,8-dihydroxy-1,4-naphthoquinone, 2-methoxy-5,6,8-trihydroxy-1,4-naphthoquinone, 2,5-dimethoxy-1,4-naphthoquinone, 2,6-dimethoxy-1,4-naphthoquinone, 2,5,8-trimethoxy-1,4-naphthoquinone, 2-chloro-5-methyl-1,4-naphthoquinone, 2-chloro-6-methyl-1,4-naphthoquinone, 2-chloro-6,7-dimethyl-1,4-naphthoquinone, 2-chloro-5-butyl-1,4-naphthoquinone, 2-chloro-6-butyl-1,4-naphthoquinone, 2-chloro-6,7-dibutyl-1,4-naphthoquinone, 2-chloro-5-pentyl-1,4-naphthoquinone, 2-chloro-6-pentyl-1,4-naphthoquinone, 2,5-dichloro-1,4-naphthoquinone, 2,6-dichloro-1,4-naphthoquinone, 2,6,7-trichloro-1,4-naphthoquinone, 2-chloro-5-hydroxy-1,4-naphthoquinone, 2-chloro-6-hydroxy-1,4-naphthoquinone, 2-chloro-5,8-dihydroxy-1,4-naphthoquinone, 2-chloro-5,6,8-trihydroxy-1,4-naphthoquinone, 2-chloro-5-methoxy-1,4-naphthoquinone, 2-chloro-6-methoxy-1,4-naphthoquinone, 2-chloro-5,8-dimethoxy-1,4-naphthoquinone, 2-amino-5-methyl-1,4-naphthoquinone, 2-amino-6-methyl-1,4-naphthoquinone, 2-amino-6,7-dimethyl-1,4-naphthoquinone, 2-amino-5-butyl-1,4-naphthoquinone, 2-amino-6-butyl-1,4-naphthoquinone, 2-amino-6,7-dibutyl-1,4-naphthoquinone, 2-amino-5-pentyl-1,4-naphthoquinone, 2-amino-6-pentyl-1,4-naphthoquinone, 2-amino-5-chloro-1,4-naphthoquinone, 2-amino-6-chloro-1,4-naphthoquinone, 2-amino-6,7-dichloro-1,4-naphthoquinone, 2-amino-5-hydroxy-1,4-naphthoquinone, 2-amino-6-hydroxy-1,4-naphthoquinone, 2-amino-5,8-dihydroxy-1,4-naphthoquinone, 2-amino-5,6,8-trihydroxy-1,4-naphthoquinone, 2-amino-5-methoxy-1,4-naphthoquinone, 2-amino-6-methoxy-1,4-naphthoquinone and 2-amino-5,8-dimethoxy-1,4-naphthoquinone may, for example, be mentioned.

Further, as a compound of the formula (4) wherein Y and Z are a hydroxy group, an alkyl group, an alkoxy group, an amino group or a halogen atom, the following compounds may be mentioned. For example, 2,3-dimethyl-1,4-naphthoquinone, 2,3-diethyl-1,4-naphthoquinone, 2-methyl-3-hydroxy-1,4-naphthoquinone, 2-methyl-3-methoxy-1,4-naphthoquinone, 2,3-dihydroxy-1,4-naphthoquinone, 2,3-dimethoxy-1,4-naphthoquinone, 2,3-dichloro-1,4-naphthoquinone, 2-amino-3-chloro-1,4-naphthoquinone, 2,3,6-trimethyl-1,4-naphthoquinone, 2,3,6,7-tetramethyl-1,4-naphthoquinone, 2,3-dimethyl-5-butyl-1,4-naphthoquinone, 2,3-dimethyl-6-butyl-1,4-naphthoquinone, 2,3-dimethyl-6,7-dibutyl-1,4-naphthoquinone, 2,3-dimethyl-5-pentyl-1,4-naphthoquinone, 2,3-dimethyl-6-pentyl-1,4-naphthoquinone, 2,3-dimethyl-5-chloro-1,4-naphthoquinone, 2,3-dimethyl-6-chloro-1,4-naphthoquinone, 2,3-dimethyl-6,7-dichloro-1,4-naphthoquinone, 2,3-dimethyl-5-hydroxy-1,4-naphthoquinone, 2,3-dimethyl-6-hydroxy-1,4-naphthoquinone, 2,3-dimethyl-5,8-dihydroxy-1,4-naphthoquinone, 2,3-dimethyl-5,6,8-trihydroxy-1,4-naphthoquinone, 2,3-dimethyl-5-methoxy-1,4-naphthoquinone, 2,3-dimethyl-6-methoxy-1,4-naphthoquinone, 2,3-dimethyl-5,8-dimethoxy-1,4-naphthoquinone, 2,6-dimethyl-3-hydroxy-1,4-naphthoquinone, 2,6,7-trimethyl-3-hydroxy-1,4-naphthoquinone, 2-methyl-3-hydroxy-5-butyl-1,4-naphthoquinone, 2-methyl-3-hydroxy-6-butyl-1,4-naphthoquinone, 2-methyl-3-hydroxy-6,7-dibutyl-1,4-naphthoquinone, 2-methyl-3-hydroxy-5-pentyl-1,4-naphthoquinone, 2-methyl-3-hydroxy-6-pentyl-1,4-naphthoquinone, 2-methyl-3-hydroxy-5-chloro-1,4-naphthoquinone, 2-methyl-3-hydroxy-6-chloro-1,4-naphthoquinone, 2-methyl-3-hydroxy-6,7-dichloro-1,4-naphthoquinone, 2-methyl-3,5-dihydroxy-1,4-naphthoquinone, 2-methyl-3,6-dihydroxy-1,4-naphthoquinone, 2-methyl-3,5,8-trihydroxy-1,4-naphthoquinone, 2-methyl-3,5,6,8-tetrahydroxy-1,4-naphthoquinone, 2-methyl-3-hydroxy-5-methoxy-1,4- naphthoquinone, 2-methyl-3-hydroxy-6-methoxy-1,4-naphthoquinone, 2-methyl-3-hydroxy-5,8-dimethoxy-1,4-naphthoquinone, 2,3-dichloro-6-methyl-1,4-naphthoquinone, 2,3-dichloro-6,7-dimethyl-1,4-naphthoquinone, 2,3-dichloro-5-butyl-1,4-naphthoquinone, 2,3-dichloro-6-butyl-1,4-naphthoquinone, 2,3-dichloro-6,7-dibutyl-1,4-naphthoquinone, 2,3-dichloro-5-pentyl-1,4-naphthoquinone 2,3-dichloro-6-pentyl-1,4-naphthoquinone, 2,3,5-trichloro-1,4-naphthoquinone, 2,3,6-trichloro-1,4-naphthoquinone, 2,3,6,7-tetrachloro-1,4-naphthoquinone, 2,3-dichloro-5-hydroxy-1,4-naphthoquinone, 2,3-dichloro-6-hydroxy-1,4-naphthoquinone, 2,3-dichloro-5,8-dihydroxy-1,4-naphthoquinone, 2,3-dichloro-5,6,8-trihydroxy-1,4-naphthoquinone, 2,3-dichloro-5-methoxy-1,4-naphthoquinone, 2,3-dichloro-6-methoxy-1,4-naphthoquinone, 2,3-dichloro-5,8-dimethoxy-1,4-naphthoquinone, 2-amino-3-chloro-6-methyl-1,4-naphthoquinone, 2-amino-3-chloro-6,7-dimethyl-1,4-naphthoquinone, 2-amino-3-chloro-5-butyl-1,4-naphthoquinone, 2-amino-3-chloro-6-butyl-1,4-naphthoquinone, 2-amino-3-chloro-6,7-dibutyl-1,4-naphthoquinone, 2-amino-3-chloro-5-pentyl-1,4-naphthoquinone, 2-amino-3-chloro-6-pentyl-1,4-naphthoquinone, 2-amino-3-chloro-5-chloro-1,4-naphthoquinone, 2-amino-3,6-dichloro-1,4-naphthoquinone, 2-amino-3,6,7-trichloro-1,4-naphthoquinone, 2-amino-3-chloro-5-hydroxy-1,4-naphthoquinone, 2-amino-3-chloro-6-hydroxy-1,4-naphthoquinone, 2-amino-3-chloro-5,8-dihydroxy-1,4-naphthoquinone, 2-amino-3-chloro-5,6,8-trihydroxy-1,4-naphthoquinone, 2-amino-3-chloro-5-methoxy-1,4-naphthoquinone, 2-amino-3-chloro-6-methoxy-1,4-naphthoquinone and 2-amino-3-chloro-5,8-dimethoxy-1,4-naphthoquinone may, for example, be mentioned.

Now, specific examples of the compound represented by the following formula (5) will be described.

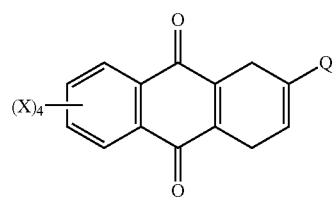

(5)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, and Q is a hydrogen atom, a $C_{1-15}$ alkyl group or a halogen atom.

As specific examples of the compound of the formula (5), 1,4-dihydro-9,10-anthraquinone, 2-methyl-1,4-dihydro-9,10-anthraquinone, 2-chloro-1,4-dihydro-9,10-anthraquinone, 6-methyl-1,4-dihydro-9,10-anthraquinone, 2,6-dimethyl-1,4-dihydro-9,10-anthraquinone, 2-chloro-6-methyl-1,4-dihydro-9,10-anthraquinone and 2,6-dichloro-1,4-dihydro-9,10-anthraquinone may, for example, be mentioned.

Now, specific examples of the compound represented by the following formula (6) will be described.

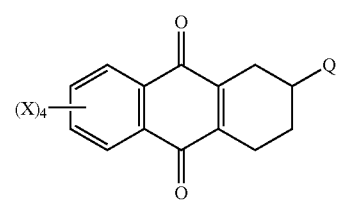

(6)

wherein X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a Ce-12 aryloxy group or a halogen atom, and Q is a hydrogen atom, a $C_{1-15}$ alkyl group or a halogen atom.

As specific examples of the compound represented by the formula (6), 1,2,3,4-tetrahydro-9,10-anthraquinone, 2-methyl-1,2,3,4-tetrahydro-9,10-anthraquinone, 2-chloro-1,2,3,4-tetrahydro-9,10-anthraquinone, 6-methyl-1,2,3,4-tetrahydro-9,10-anthraquinone, 2,6-dimethyl-1,2,3,4-tetrahydro-9,10-anthraquinone, 2-chloro-6-methyl-1,2,3,4-tetrahydro-9,10-anthraquinone and 2,6-dichloro-1,2,3,4-tetrahydro-9,10-anthraquinone may, for example, be mentioned.

The compounds represented by the formulae (1) to (3) of the present invention are easily prepared by subjecting the corresponding hydroxynaphthalene compound or hydroxyanthracene compound to alkylation by an alkylating agent, arylation by an arylating agent, hydroxyalkylation by an alkylene oxide, acylation by an acylating agent or substituted-carbonylation by a substituted carbonylating agent.

Many naphthoquinone compounds having a substituent at the 2-position represented by the formula (4) are available as reagents, or they may be obtained by reacting a 1,4-naphthoquinone compound and a corresponding nucleophilic reagent to obtain a hydroquinone compound substituted at the 2-position, followed by oxidation treatment. For example, they may be prepared e.g. by the method disclosed in Experimental chemistry lecture 15, Organic Compound Synthesis III, aldehyde/ketone/quinone, 5th edition (The Chemical Society of Japan), page 369 and 384.

Further, the compounds of the formulae (5) and (6) may be prepared by subjecting a 1,4-naphthoquinone compound and a corresponding butadiene compound to Diels Alder reaction to form a cyclic adduct, which is isomerized and oxidized, or further by subjecting the oxidized product to catalytic hydrogen reduction.

Among the above-mentioned specific examples, as the compound of the formula (1), 4-methoxy-1-naphthol, 4-ethoxy-1-naphthol, 1,4-dimethoxynaphthalene, 1,4-diethoxynaphthalene, 1,4-di-n-propoxynaphthalene, 1,4-diisopropoxynaphthalene, 1,4-di-n-butoxynaphthalene, 1,4-dihexyloxynaphthalene and 1,4-bis(2-ethylhexyloxy) naphthalene may be mentioned. As the compound of the formula (2), 9,10-dimethoxyanthracene, 9,10-diethoxyanthracene, 9,10-di-n-propoxyanthracene, 9,10-diisopropoxyanthracene, 9,10-di-n-butoxyanthracene, 9,10-bis(2-ethylhexyloxy)anthracene, 9,10-didodecyloxyanthracene, 9,10-bis(acetyloxy)anthracene, 9,10-bis(propionyloxy)anthracene, 9,10-bis(n-butyryloxy)anthracene, 9,10-bis(i-butyryloxy)anthracene, 9,10-bis(n-pentanoyloxy) anthracene, 9,10-bis(n-hexanoyloxy)anthracene, 9,10-bis(n-heptanoyloxy)anthracene, 9,10-bis(n-octanoyloxy) anthracene, 9,10-bis(2-ethylhexanoyloxy)anthracene, 9,10-bis(n-nonanoyloxy)anthracene, 9,10-bis(methoxycarbonyloxy)anthracene, 9,10-bis (ethoxycarbonyloxy)anthracene, 9,10-bis(n-propoxycarbonyloxy)anthracene, 9,10-bis(i-propoxycarbonyloxy)anthracene, 9,10-bis(n-butoxycarbonyloxy)anthracene, 9,10-bis(n-pentoxycarbonyloxy)anthracene, 9,10-bis(n-hexyloxycarbonyloxy)anthracene, 9,10-bis(n-heptyloxycarbonyloxy)anthracene, 9,10-bis(n-octyloxycarbonyloxy)anthracene, 9,10-bis(2-ethylhexyloxycarbonyloxy)anthracene and 9,10-bis(n-nonyloxycarbonyloxy)anthracene may be mentioned. As the compound of the formula (3), 9-methoxyanthracene, 9-ethoxyanthracene, 9-n-propoxyanthracene, 9-isopropoxyanthracene, 9-n-butoxyanthracene, 9-(2-ethylhexyloxy)anthracene and 9-dodecyloxyanthracene may be mentioned. As the compound of the formula (4), 1,4-naphthoquinone, 2-methyl-1,4-naphthoquinone, 2-ethyl-1,4-naphthoquinone, 2-hydroxy-1,4-naphthoquinone, 2-methoxy-1,4-naphthoquinone and 2-chloro-1,4-naphthoquinone may be mentioned. As the compound of the formula (5), 1,4-dihydro-9,10-anthraquinone and 2-methyl-1,4-dihydro-9,10-anthraquinone may be mentioned. As the compound of the formula (6), 1,2,3,4-tetrahydro-9,10-anthraquinone and 2-methyl-1,2,3,4-tetrahydro-9,10-anthraquinone may be mentioned. Among them, in view of easiness of production, preferred are 4-methoxy-1-naphthol, 4-ethoxy-1-naphthol, 1,4-dimethoxynaphthalene, 1,4-diethoxynaphthalene, 9,10-dimethoxyanthracene, 9,10-diethoxyanthracene, 9,10-di-n-propoxyanthracene, 9,10-diisopropoxyanthracene, 9,10-di-n-butoxyanthracene, 9,10-bis(n-butyryloxy), 9,10-bis(n-heptanoyloxy)anthracene, 9,10-bis(n-octanoyloxy)anthracene, 9,10-bis(n-butoxycarbonyloxy)anthracene, 9-isopropoxyanthracene, 9-n-butoxyanthracene, 1,4-naphthoquinone, 2-methyl-1,4-naphthoquinone, 2-hydroxy-1,4-naphthoquinone and 2-methoxy-1,4-naphthoquinone. Particularly preferred are 4-methoxy-1-naphthol, 4-ethoxy-1-naphthol, 1,4-diethoxynaphthalene, 9,10-di-n-propoxyanthracene, 9,10-di-n-butoxyanthracene, 9,10-bis(n-octanoyloxy)anthracene, 1,4-naphthoquinone, 2-methyl-1,4-naphthoquinone and 2-hydroxy-1,4-naphthoquinone.

[Radical Polymerizable Composition]

The radical polymerizable composition of the present invention comprises the radical polymerization control agent of the present invention and a radical polymerizable compound. By the radical polymerization control agent of the present invention, if radical species are generated in the radical polymerizable composition by an influence of heat or the like, the radical species are scavenged by the radical polymerization control agent of the present invention to inhibit radical polymerization of the radical polymerizable compound from being initiated. That is, storage stability of the radical polymerizable compound is accomplished. However, when the radical polymerizable compound is to be radical-polymerized, by irradiating the composition with light at a specific wavelength (light containing light within a wavelength range of from 300 nm to 500 nm), the radical polymerization control agent of the present invention becomes inactive to radicals, whereby radical polymerization can be initiated. That is, the radical polymerization control agent of the present invention can control initiation and termination of radical polymerization by irradiation with light at a certain specific wavelength. Further, it can control initiation and inhibition of polymerization by whether the composition is irradiated with light or not.

The difference between the radical polymerization control agent of the present invention and the photoradical polymerization initiator is as follows. That is, the photoradical polymerization initiator has an ability to initiate radical polymerization by irradiation with light at a specific wavelength (light conditions), but is inactive to radicals under dark conditions (under conditions not irradiated with light at a specific wavelength). On the other hand, the radical polymerization control agent of the present invention is active to radicals, has an ability to scavenge generated radicals and has a role as a radical polymerization inhibitor under dark conditions (conditions not irradiated with light at a specific wavelength), but loses the ability to scavenge radicals and becomes inactive by irradiation with light at a specific wavelength. They are the same in that they will not initiate polymerization under dark conditions and bring about polymerization under light conditions, but totally differ in the essentiality of the action.

The radical polymerization control agent of the present invention may be preliminarily added to the radical polymerizable compound so that it is used as a storage stabilizer for the radical polymerizable compound, or may be added to the radical polymerizable compound when radical polymerization is to be initiated for the purpose of controlling polymerization by irradiation with light at a specific wavelength.

The amount of the radical polymerization control agent of the present invention blended is, in view of sufficient radical polymerization inhibiting effect and economical efficiency, usually preferably from 0.1 to 10 parts by weight per 100 parts by weight of the radical polymerizable compound, more preferably from 0.2 to 5 parts by weight.

[Radical Polymerizable Compound]

The radical polymerizable compound in the present invention is not particularly limited so long as it is a compound having a polymerizable double bond in its molecule.

Such a radical polymerizable compound may, for example, be an α,β-unsaturated carboxylic acid compound such as acrylic acid or methacrylic acid; an α,β-unsaturated carboxylic acid ester compound such as methyl acrylate, ethyl acrylate, butyl acrylate, 2-ethylhexyl acrylate, octyl acrylate, 2-hydroxyethyl acrylate, 2-hydroxypropyl acrylate, methyl methacrylate or butyl methacrylate; a vinyl ester compound such as vinyl acetate; an acrylic compound such as acrylonitrile or acrylamide; an aromatic vinyl compound such as styrene, α-methylstyrene, vinyltoluene or divinylbenzene; a substituted ethylene compound such as vinyl chloride or vinylidene chloride; an ethylenic unsaturated compound such as ethylene, propylene, butene, butadiene, isoprene, cyclopentadiene or pinene; or an unsaturated organic silane compound such as 3-methacryloxypropyltrimethoxysilane, 3-methacryloxypropyltriethoxysilane or vinyl trimethoxysilane. An oligomer of the above radical polymerizable compound may also be used.

Among the radical polymerizable compounds, (meth)acrylic acid which is an α,β-unsaturated carboxylic acid compound, a (meth)acrylic acid ester which is an α,β-unsaturated carboxylic acid ester, and styrene which is an aromatic vinyl compound, are preferred.

The form and the content of the radical polymerizable compound contained in the radical polymerizable composition are not particularly limited. For example, the radical polymerizable compound as it is or a solution of the radical polymerizable compound may be mentioned.

To the radical polymerizable composition containing the radical polymerization control agent of the present invention as an essential component, a radical polymerization initiator to initiate radical reaction may be added as the case requires. And, an initiation energy such as heat or light necessary to initiate polymerization is applied to initiate polymerization, whereby a polymer can be produced. Further, by irradiation with light at a specific wavelength at the time of the polymerization reaction, initiation and termination of the polymerization reaction can be controlled.

[Radical Polymerization Initiator]

The radical polymerization initiator is not particularly limited so long as it generates radicals active to the radical polymerizable compound by applying an energy thereto. Usually, a commercially available so-called radical polymerization initiator may be used. Usually, for convenience, one which is used by applying a heat energy will be called a thermal radical polymerization initiator, and one which is used by applying a light energy will be called a photoradical polymerization initiator. In the present invention, both the thermal radical polymerization initiator and the photoradical polymerization initiator may be used.

The thermal radical polymerization initiator is not particularly limited, and a known compound may be used. For example, a peroxide, a hydroperoxide or an azo compound may be mentioned. Specifically, a peroxide such as benzoyl peroxide, di-t-amyl peroxide, t-butyl peroxybenzoate, 2,5-dimethyl-2,5-di-(t-butyl peroxy)hexane, 2,5-dimethyl-2,5-di-(t-butyl peroxy)hexine-3 or di-cumyl peroxide, a hydroperoxide such as t-amyl hydroperoxide, t-butyl hydroperoxide or hydrogen peroxide, or an azo compound such as 2,2'-azobis(2,4-dimethylpentanenitrile), 2,2'-azobis(2-methylpropanenitrile), 2,2'-azobis(2-methylbutanenitrile) or 2,2'-azobis(cyclohexanecarbonitrile) may be mentioned.

Further, in order to use the thermal radical polymerization initiator at a relatively low temperature, a so-called redox initiator using a reducing agent such as a transition metal or an amine in combination with an oxidizing agent initiator such as a peroxide, a hydroperoxide or ascorbic acid may be used.

The photoradical polymerization initiator is not particularly limited, and a known compound may be used. For example, a benzoin compound, an acetophenone, a benzophenone, a thioxanthone, an a-acyloxime ester, a phenylglyoxylate, a benzyl, an azo compound, a diphenylsulfide compound, an acylphosphine oxide compound, an organic dye compound, an iron-phthalocyanine, a benzoin, a benzoin ether or an anthraquinone may be used. Specifically, a benzoin such as benzoin, benzoin methyl ether, benzoin ethyl ether, benzoin propyl ether or benzoin isobutyl ether; an acetophenone such as acetophenone, 2,2-diethoxy-2-phenylacetophenone, 1,1-dichloroacetophenone, 2-hydroxy-2-methyl-phenylpropan-1-one, diethoxyacetophenone, 1-hydroxycyclohexyl phenyl ketone or 2-methyl-1-[4-methylthio)phenyl]-2-morpholinopropan-1-one, an anthraquinone such as 2-ethylanthraquinone, 2-t-butylanthraquinone; 2-chloroantraquinone or 2-amylanthraquinone; a thioxanthone such as 2,4-diethylthioxanthone, 2-isopropylthioxanethone or 2-chlorothioxanthone; a ketal such as acetophenone dimethyl ketal or benzyl dimethyl ketal; a benzophenone such as benzophenone, 4-benzoyl-4'-methyldiphenyl sulfide or 4,4'-bismethylaminobenzophenone; or a phosphine oxide such as 2,4,6-trimethylbenzoyl diphenylphosphine oxide or bis(2,4,6-trimethylbenzoyl)-phenylphosphine oxide may be mentioned. A photoradical polymerization initiator disclosed in known literature such as Journal of The Society of Synthetic Organic Chemistry, Japan, 66, 458 (2008) may also be used.

Further, as a commercially available photoradical polymerization initiator, an acylphosphine oxide compound such as 1-hydroxycyclohexyl phenyl ketone (Irgacure 184 manufactured by Ciba Specialty Chemicals, Irgacure is a registered trademark of Ciba Specialty Chemicals), (2-methyl-1-(4-methylthio)phenyl)-2-(4-morpholinyl)-1-propanone) (Irgacure 907) or bis(2,4,6-trimethylbenzoyl)-diphenylphosphine oxide (Irgacure 819); a titanocene compound such as bis($\eta^5$-2,4-cyclopentadien-1-yl)-bis(2,6-difluoro-3-(1H-pyrrol-1-yl)-phenyl)titanium (Irgacure 784): or a naphthacenequinone compound such as 6,12-bis(trimethylsilyloxy)-1,11-naphthacenequinone may, for example, be mentioned.

Such a radical polymerization initiator may be used alone or in combination of two or more. The thermal radical polymerization initiator and the photoradical polymerization initiator may be used in combination. The amount of the radical polymerization initiator added depends on the radical polymerizable compound and the radical polymerization control agent used, and is preferably within a range of at least 0.0001 part by mass and at most 10 parts by mass per 100 parts by mass of the total amount of the radical polymerizable compound.

[Polymerization Initiation Energy]

The polymerization initiation energy may be an energy which can generate radicals from the radical initiator added. Usually, a thermal energy or an electromagnetic energy may be properly selected. As a specific energy source, heat or electromagnetic radiations such as light, electron beams (EB), microwaves or radioactive rays may be mentioned, and polymerization may be called e.g. thermal polymerization or electromagnetic polymerization (photopolymerization, electron beam polymerization, microwave polymerization or radiation polymerization), etc. in accordance with the energy source used.

[Thermal Polymerization]

In the case of thermal polymerization, the temperature range for polymerization is usually from −20 to 200° C., preferably from 0 to 150° C., more preferably from 10 to 120° C., although it depends on the radical polymerizable compound used and its embodiment.

Further, as one type of thermal polymerization, redox polymerization employing an oxidation-reduction (redox) initiator (as described hereinafter) may be mentioned. In such a case, the temperature range is lower than conventional thermal polymerization and is from −40 to 100° C., preferably from −20 to 80° C., more preferably from 0 to 60° C.

To the radical polymerizable composition containing the radical polymerization control agent of the present invention and a radical polymerizable compound, a radical polymerization initiator is added and an initiation energy is applied, whereby polymerization of the radical polymerizable compound is initiated. When the initiation energy is applied, in a state without irradiation with light within a wavelength range of from 300 to 500 nm, radicals generated by the radical polymerization initiator are scavenged by the radical polymerization control agent of the present invention and polymerization is inhibited. Accordingly, in order to initiate radical polymerization, it is necessary to add a radical polymerization initiator more than necessary so as to generate radicals in an amount exceeding the scavenging power of the radical polymerization control agent. However, by conducting initiation of radical polymerization under irradiation with light within a wavelength range of from 300 to 500 nm, the radical scavenging power of the radical polymerization control agent is lost, and the radical polymerization can be initiated by addition of a radical polymerization initiator in a small amount.

Further, the radical polymerizable composition containing a thermal radical polymerization initiator and the radical polymerization control agent of the present invention is applied into a film, and the resulting coating film is covered with a light shielding film having a pattern, and the radical polymerizable composition is heated under irradiation with light within a wavelength range of from 300 to 500 nm, whereby polymerization proceeds only in a portion exposed to light, and polymerization reaction does not sufficiently proceed in a portion not exposed to light, and a pattern of a polymer can be formed. That is, a pattern of a polymer usually formed by a photopolymerization initiator can be formed by a thermal polymerization initiator.

Further, when a thermal energy is applied to the radical polymerizable composition containing a thermal radical polymerization initiator and the radical polymerization control agent of the present invention to conduct radical polymerization, by irradiating a specific region of the radical polymerizable composition with light rays containing light within a wavelength range of from 300 nm to 500 nm, radical polymerization proceeds only in the specific region.

Light within a specific wavelength range to be applied at the time of the polymerization reaction may be light rays containing light within a wavelength range of from 300 to 500 nm. A light source may be any light source which can apply light rays within a wavelength range of from 300 to 500 nm. For example, a LED (light emitting diode) or a lamp may be used. The LED may, for example, be UV-LED, blue LED or white LED. The lamp may, for example, be a high pressure mercury lamp, an ultrahigh pressure mercury lamp, a halogen lamp or a metal halide lamp.

In the case of the radical polymerization control agent of the present invention represented by any one of the formulae (1) and (4) to (6), among light rays containing light within a wavelength range of from 300 to 500 nm, light rays containing light within a wavelength range of from 300 to 370 nm are preferred, and in the case of the radical polymerization control agent of the present invention represented by the formula (2) or (3), light rays containing light within a wavelength range of from 350 to 500 nm are preferred.

The irradiation intensity may be at a level of from 1 to 2,000 mW/cm$^2$.

[Photopolymerization]

The polymerization reaction employing the radical polymerization control agent of the present invention may be applicable also to photopolymerization. In photopolymerization, as light to be applied, ultraviolet rays, visible rays or infrared rays may, for example, be used. In addition to the radical polymerization control agent of the present invention, a photoradical polymerization initiator is used, and a photopolymerization sensitizer may also be used. Specifically, a radical polymerizable composition containing the radical polymerization control agent of the present invention, a radical polymerizable compound and a photoradical polymerization initiator is prepared, and as a polymerization initiation energy, light such as ultraviolet rays or visible rays is applied to initiate polymerization. On that occasion, by irradiation with light within a wavelength range of from 300 to 500 nm at the same time, it is possible to inactivate the radical polymerization control agent of the present invention, and it is not necessary to add an unnecessary photoradical polymerization initiator.

In the case of ultraviolet rays or visible rays, specifically, for example, light rays within a wavelength range of from 300 to 800 nm are used. As a light source, a LED (light emitting diode) or a lamp which can apply light rays within a wavelength range of from 300 to 800 nm is used. The LED may, for example, be a UV-LED, a blue LED or a white LED. The lamp may, for example, be a high pressure mercury lamp, an ultrahigh pressure mercury lamp, a halogen lamp or a metal halide lamp.

Electron beam polymerization is carried out by irradiation with electron beams. For electron beam irradiation, any method which acts on the electron beam polymerizable compound and brings about polymerization of the polymerizable compound may be employed. The quantity of the electron beams applied is preferably adjusted within a range of from about 1 to about 300 kGy as the absorbed dose. If it is less than 1 kGy, no sufficient irradiation effect can be obtained, and irradiation exceeding 300 kGy may deteriorate the substrate. As a method of applying electron beams, for example, a scanning method, a curtain beam method or a broad beam method may, for example, be employed, and the accelerating voltage at the time of applying electron beams should be controlled by the thickness of the substrate to be irradiated and is appropriately from about 20 to about 100 kV.

For microwave polymerization, a known means by Strauss et al. (Aust. J. Chem., 48, 1,665 to 1,692 (1995)) may be employed. Microwaves may be generated by any of various methods known in microwave technology. In general, such a method depends on klystron or magnetron used as a microwave generation source. Usually, the generation frequency is within a range of from about 300 MHz to about 30 GHz, and the corresponding wavelength is from about 1 m to about 1 mm. Theoretically, any frequency within this range can be effectively used, but it is preferred to employ frequency within a commercially available range including from about 850 to about 950 MHz or from about 2,300 to about 2,600 MHz.

For radiation polymerization, polymerization is carried out by irradiation with γ rays, X rays, α rays or β rays. Usually, irradiation with cobalt 60 γ rays is employed in many cases.

Also in the case of the photoradical polymerization initiator, a radical polymerizable composition containing a photoradical polymerization initiator and the radical polymerization control agent of the present invention is applied into a film, and the resulting coating film is covered with a light shielding film having a pattern, and a light energy (electromagnetic energy) to activate the photoradical polymerization initiator is applied to the radical polymerizable composition under irradiation with light within a wavelength range of from 300 to 500 nm to initiate polymerization, whereby polymerization proceeds only in a portion exposed to light within a wavelength range of from 300 to 500 nm, and polymerization reaction does not sufficiently proceed in a portion not exposed to light within a wavelength range of from 300 to 500 nm, whereby a pattern of a polymer can be formed.

In a case where light having a light energy applied in the photopolymerization is light having a wavelength within a range of from 300 to 500 nm, initiation of photopolymerization and inactivation of the radical polymerization control agent of the present invention occur simultaneously.

For example, a radical polymerizable composition containing a photoradical polymerization initiator and the radical polymerization control agent of the present invention is applied into a film, and the resulting coating film is covered with a light shielding film having a pattern, and polymerization of the radical polymerizable composition is initiated under irradiation with light within a wavelength range of from 300 to 500 nm, polymerization proceeds only in a portion exposed to light, whereby a pattern of a polymer can be formed. This reaction is a reaction which proceeds even when the radical polymerization control agent of the present invention is not contained, however, in this reaction, if a conventional radical polymerization inhibitor is contained in the radical polymerizable composition, not the radical polymerization control agent of the present invention, the lead time for the radical polymerization may be long, or the polymerization reaction does not smoothly proceed unless the amount of the photoradical polymerization initiator added is increased. However, by the radical polymerizable composition containing the radical polymerization control agent of the present invention, not the polymerization inhibitor, storage stability of the radical polymerizable compound is secured and at the same time, the radical polymerization will smoothly proceed, and the amount of the radical polymerization initiator added is small. Further, when light application is focused or when photopolymerization is carried out with a part of the composition shielded from light, the radical polymerization control agent of the present invention acts as a radical polymerization inhibitor at a portion not exposed to light, whereby a boundary between a part irradiated with light and a part not irradiated with light will be sharp.

Further, also in a case where a radical polymerizable composition containing a photoradical polymerization initiator and the radical polymerization control agent of the present invention is subjected to radical polymerization by applying a light energy, by irradiating a specific region of the radical polymerizable composition with light rays containing light within a wavelength range of from 300 nm to 500 nm, it is possible that radical polymerization proceeds only in the specific region.

[Other Component]

For radical polymerization of the radical polymerizable composition containing the radical polymerization control agent of the present invention and a radical polymerizable compound, in addition to the radical polymerization control agent of the present invention, the radical polymerizable compound and the radical polymerization initiator, as the case requires, other components may be incorporated within a range not to impair the effects of the present invention, and a solvent, a coloring agent, a plasticizer, a tackifier, an antioxidant, a stabilizer, a filler, a surfactant, a coupling agent, an antistatic agent, an ultraviolet absorber, etc. may be added.

EXAMPLES

Now, the present invention will be described in further detail with reference to Examples. However, Examples are merely exemplified as Examples. That is, the following Examples are not exhaustive nor intended to restrict the present invention as described. Accordingly, the present invention is by no means restricted to the following Examples within a range not to exceed the scope of the present invention. Further, unless otherwise specified, all the parts and percentages are based on the weight.

<Photo DSC Measurement>

In this Example, photo DSC measurement was carried out as follows. As a DSC measurement apparatus, XDSC-7000 manufactured by Hitachi High-Technologies Corporation was used, and a photo DSC measurement unit was attached thereto so that DSC measurement could be conducted while applying light.

As a light source for light irradiation, LA-410UV manufactured by HAYASHI-REPIC CO. LTD. was used, and a band-pass filter was set so that 405 nm light or 365 nm light was taken out and applied to a sample. The light illuminance was 50 mW/cm$^2$. Light from the light source was lead to the upper part of the sample by glass fibers, and the shutter of the light source was trigger controlled so that the DSC measurement could be started simultaneously with initiation of light irradiation.

For photo DSC measurement, about 1 mg of a sample was accurately weighed in a measurement aluminum pan, which was put in a DSC measurement part, and the photo DSC unit was attached. Then, the interior of the measurement part was heated to a measurement temperature and at the same time replaced with nitrogen over a period of 5 minutes, and measurement was started. Measurement was continued for 10 minutes while ordinary light was applied. After the first measurement, measurement was conducted again under the same conditions while the sample was as it was, and a value obtained by subtracting the second measurement result from the first measurement result was taken as the measurement result of the sample. The result was the total heating value per 1 mg of a sample in ten minutes after light irradiation, unless otherwise specified. In a case where light was not applied, measurement was carried out once for 100 minutes at a constant measurement temperature, and whether heat generation occurred or not was confirmed.

When polymerization of the sample (radical polymerizable composition) occurs accompanying light irradiation, a heat of reaction accompanying the polymerization is generated, and the heat of reaction can be measured by photo DSC. Thus, the degree of progress of polymerization by light irradiation can be measured by photo DSC. In this Example, the total heating value in ten minutes after light irradiation was measured, and when the heating value was measured and the radical polymerizable compound was changed from liquid to solid as confirmed by touching the sample with fingers after measurement, it is considered that the polymerization reaction proceeded.

Example 1

10 g of trimethylpropane triacrylate, 5 mg (500 ppm) of 4-methoxy-1-naphthol (MNT) as a radical polymerization control agent and 25 mg (2,500 ppm) of azobisisobutyronitrile as a radical initiator were mixed to obtain a radical polymerizable composition. About 1 mg of the radical polymerizable composition was accurately weighed and put in a measurement aluminum pan, and irradiated with light at a wavelength of 365 nm with an illuminance of 50 mW/cm$^2$, while the temperature was kept at 60° C., to conduct photo DSC measurement of the radical polymerizable composition, whereupon the total heating value in 10 minutes from initiation of light irradiation was 322 mJ/mg. Further, the radical polymerizable composition was changed from liquid to solid as confirmed by touching with fingers. The results are shown in Table 1.

Example 2

A radical polymerizable composition was prepared in the same manner as in Example 1 and put in an aluminum pan, and the temperature was kept at 60° C. without irradiation with light, whereupon no heat generation was observed, and the radical polymerizable composition remained in a liquid state. The results are shown in Table 1.

Example 3

The measurement was carried out in the same manner as in Example 1 except that 50 mg (5,000 ppm) of 2-hydroxy-1,4-naphthoquinone (LSN) was used instead of 4-methoxy- 1-naphthol (MNT), and the amount of azobisisobutyronitrile was changed to 2.5 mg (250 ppm). As a result, the total heating value in 10 minutes from initiation of light irradiation was 353 mJ/mg. Further, the radical polymerizable composition was changed from liquid to solid as confirmed by touching with fingers. The results are shown in Table 1.

Example 4

In the same manner as in Example 3, a radical polymerizable composition was prepared and put in an aluminum pan, and the temperature was kept at 60° C. without irradiation with light, whereupon no heat generation was observed, and the radical polymerizable composition remained in a liquid state. The results are shown in Table 1.

Example 5

The measurement was carried out in the same manner as in Example 1 except that 25 mg (2,500 ppm) of 9,10-diethoxyanthracene (DEA) was used instead of 4-methoxy-1-naphthol (MNT), the amount of azobisisobutyronitrile was changed to 2.5 mg (250 ppm) and the wavelength of light applied was changed to 405 nm. As a result, the total heating value in ten minutes from initiation of light irradiation was 586 mJ/mg. Further, the radical polymerizable composition was changed from liquid to solid as confirmed by touching with fingers. The results are shown in Table 1.

Example 6

In the same manner as in Example 5, a radical polymerizable composition was prepared and put in an aluminum pan, and the temperature was kept at 60° C. without irradiation with light, whereupon no heat generation was observed, and the radical polymerizable composition remained in a liquid state. The results are shown in Table 1.

Example 7

The measurement was carried out in the same manner as in Example 1 except that 25 mg (2,500 ppm) of 9,10-dibutoxyanthracene (DBA) was used instead of 4-methoxy-1-naphthol (MNT), the amount of azobisisobutyronitrile was changed to 2.5 mg (250 ppm) and the wavelength of light applied was changed to 405 nm. As a result, the total heating value in ten minutes from initiation of light irradiation was 333 mJ/mg. Further, the radical polymerizable composition was changed from liquid to solid as confirmed by touching with fingers. The results are shown in Table 1.

Example 8

In the same manner as in Example 7, a radical polymerizable composition was prepared and put in an aluminum pan, and the temperature was kept at 60° C. without irradiation with light, whereupon no heat generation was observed, and the radical polymerizable composition remained in a liquid state. The results are shown in Table 1.

Example 9

The measurement was carried out in the same manner as in Example 1 except that 25 mg (2,500 ppm) of 9,10-bis(n-octanoyloxy)anthracene (OcA) was used instead of 4-methoxy-1-naphthol (MNT), the amount of azobisisobutyronitrile was changed to 2.5 mg (250 ppm) and the wavelength of light applied was changed to 405 nm. As a result, the total heating value in ten minutes from initiation of light irradiation was 262 mJ/mg. Further, the radical polymerizable composition was changed from liquid to solid as confirmed by touching with fingers. The results are shown in Table 1.

Example 10

In the same manner as in Example 3, a radical polymerizable composition was prepared and put in an aluminum pan, and the temperature was kept at 60° C. without irradiation with light, whereupon no heat generation was observed, and the radical polymerizable composition remained in a liquid state. The results are shown in Table 1.

Comparative Example 1

The measurement was carried out in the same manner as in Example 1 except that no radical polymerization control agent was added. As a result, the total heating value in ten minutes from initiation of light irradiation was 125 mJ/mg. Further, the radical polymerizable composition was changed from liquid to semisolid as confirmed by touching with fingers, however, the polymerization reaction did not sufficiently proceed. The results are shown in Table 1.

TABLE 1

| | Radical polymerization control agent | Radical polymerization initiator | Light irradiation | Total heating value (mJ/mg) | State after measurement of radical polymerizable composition (tack-free test) | Polymerization inhibiting effect of radical polymerization control agent |
|---|---|---|---|---|---|---|
| Example 1 | MNT (500 ppm) | AIBN (2,500 ppm) | 365 nm 50 mW/cm² | 322 | Solid | Nil |
| Example 2 | | | Nil | Not measured | Liquid | Observed |
| Example 3 | LSN (5,000 ppm) | AIBN (250 ppm) | 365 nm 50 mW/cm² | 353 | Solid | Nil |
| Example 4 | | | Nil | Not measured | Liquid | Observed |
| Example 5 | DEA (2,500 ppm) | AIBN (250 ppm) | 405 nm 50 mW/cm² | 586 | Solid | Nil |
| Example 6 | | | Nil | Not measured | Liquid | Observed |
| Example 7 | DBA (2,500 ppm) | AIBN (250 ppm) | 405 nm 50 mW/cm² | 333 | Solid | Nil |
| Example 8 | | | Nil | Not measured | Liquid | Observed |
| Example 9 | OcA (2,500 ppm) | AIBN (250 ppm) | 405 nm 50 mW/cm² | 262 | Solid | Nil |
| Example 10 | | | Nil | Not measured | Liquid | Observed |

TABLE 1-continued

|  | Radical polymerization control agent | Radical polymerization initiator | Light irradiation | Total heating value (mJ/mg) | State after measurement of radical polymerizable composition (tack-free test) | Polymerization inhibiting effect of radical polymerization control agent |
|---|---|---|---|---|---|---|
| Comparative Example 1 | Nil | AIBN (2,500 ppm) | 365 nm 50 mW/cm$^2$ | 125 | Semisolid | Nil |

MNT: 4-methoxy-1-naphthol
LSN: 2-hydroxy-1,4-naphthoquinone
DEA: 9,10-diethoxyanthracene
DBA: 9,10-dibutoxyanthracene
OcA: 9,10-bis(n-octanoyloxy)anthracene
AIBN: azobisisobutyronitrile As evident from Examples 2, 4, 6, 8 and 10, in the radical polymerizable composition containing a thermal radical polymerization initiator, at a temperature of 60° C. at which the radical polymerization is supposed to be initiated, by addition of the radical polymerization control agent of the present invention, initiation of radical polymerization is inhibited. It is found from these Examples that the radical polymerization control agent of the present invention has a radical polymerization inhibiting ability. On the other hand, as evident by comparison between Examples 2, 4, 6, 8 and 10 and Examples 1, 3, 5, 7 and 9, polymerization is initiated by irradiation with light at a certain specific wavelength simultaneously with heating to 60° C. That is, by irradiation of light at 365 nm or 405 nm, the radical polymerization inhibiting effect of the radical polymerization control agent of the present invention disappeared, and usual radical polymerization was conducted by radicals generated by the thermal radical polymerization initiator.

On the other hand, by comparison between Example 1 and Comparative Example 1 in which the radical polymerization control agent of the present invention is not contained, it is found that in Example 1, the total heating value is double or more the value in Comparative Example 1, no polymerization inhibiting effect by the radical polymerization control agent is observed, and polymerization is rather promoted.

The mechanism how such an effect is achieved is not clearly understood, and is considered as follows. The radical polymerization control agent of the present invention is excited by light irradiation and loses its radical scavenging power, and excited species of the radical polymerization control agent formed transfer their energy to another compound and activate the compound thereby to cause or promote a reaction to form radical species.

Example 11

10 g of trimethylpropane triacrylate, 25 mg (2,500 ppm) of 4-methoxy-1-naphthol (MNT) as a radical polymerization control agent and 25 mg (2,500 ppm) of azobisisobutyronitrile as a radical initiator were mixed to obtain a radical polymerizable composition. About 10 mg of the radical polymerizable composition was accurately weighed and put in a measurement aluminum pan, and DSC measurement was carried out under conditions at a temperature-raising rate of 3° C./min from 30° C. to 300° C. As a result, the polymerization initiation temperature was 183.4° C., and the total heating value was 475 mJ/mg. The results are shown in Table 2.

Comparative Example 2

The measurement was carried out in the same manner as in Example 11 except that the radical polymerization control agent was not added. As a result, the polymerization initiation temperature was 94.7° C., and the total heating value was 498 mJ/mg. The results are shown in Table 2.

TABLE 2

|  | Radical polymerization control agent | Radical polymerization initiator | Light irradiation | Polymerization initiation temperature (° C.) | Polymerization inhibiting effect of radical polymerization control agent |
|---|---|---|---|---|---|
| Example 11 | MNT (2,500 ppm) | AIBN (2,500 ppm) | Nil | 183.4 | Observed |
| Comparative Example 2 | Nil | AIBN (2,500 ppm) | Nil | 94.7 | Nil |

MNT: 4-methoxy-1-naphthol
AIBN: azobisisobutyronitrile

As evident from comparison between Example 11 and Comparative Example 2, in Example 11, the polymerization initiation temperature is high as compared with Comparative Example 2, and the polymerization inhibiting effect by the radical polymerization control agent of the present invention is apparently obtained in a state without light irradiation.

That is, by irradiating a radical polymerizable composition containing the radical polymerization control agent of the present invention with light at a certain specific wavelength, the radical polymerization inhibiting effect of the radical polymerization control agent disappears, and the radical polymerizable composition is polymerized and cured. A promotive effect is rather observed. On the other hand, in a case where the radical polymerizable composition is not irradiated with light at a certain specific wavelength, the polymerization inhibiting effect of the radical polymerization control agent is not lost, and the polymerization reaction does not occur, or the polymerization reaction is controlled.

INDUSTRIAL APPLICABILITY

The radical polymerization control agent of the present invention is a radical polymerization control agent which functions as a radical polymerization inhibitor in a dark place and loses the radical polymerization inhibiting effect under irradiation with light rays containing light within a wavelength range of from 300 nm to 500 nm, and does not have to be removed at the time of radical polymerization as in the case of a conventional polymerization inhibitor, and is thereby capable of providing a radical polymerization control method very useful in production.

The invention claimed is:

1. A method for controlling radical polymerization, comprising:
applying a heat energy to a radical polymerizable composition comprising a radical polymerization control agent represented by formula (1), (2), (3), (4), (5), or (6), a radical polymerizable compound, and a thermal radical polymerization initiator, thereby initiating radical polymerization of the radical polymerizable compound,
wherein the heat energy is applied while light rays containing light within a wavelength range of from 300 nm to 500 nm is irradiated to the radical polymerizable composition,

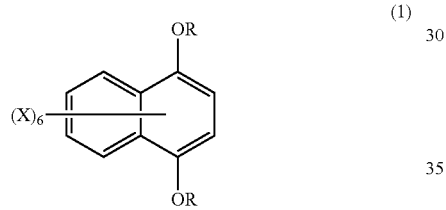
(1)

wherein in the formula (1): R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group, wherein a pair of adjacent Xs are optionally mutually bonded to form a saturated or unsaturated 6-membered ring, and the 6-membered ring formed by the pair of adjacent Xs is optionally further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

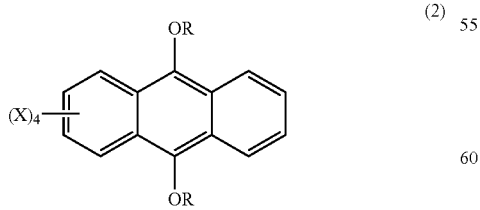
(2)

wherein in the formula (2): R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

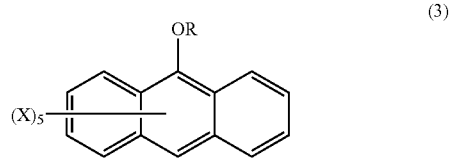
(3)

wherein in the formula (3): R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

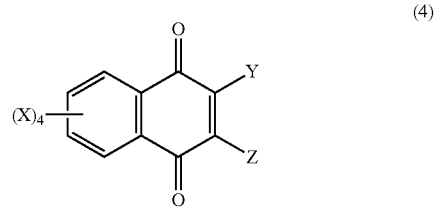
(4)

wherein in the formula (4): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, Y and Z are each independently a hydrogen atom, a hydroxy group, a $C_{1-15}$ alkyl group, a $C_{1-15}$ alkoxy group, an amino group or a halogen atom, wherein Y and Z are optionally mutually bonded to form a saturated or unsaturated 6-membered ring, and the 6-membered ring formed by Y and Z is optionally further substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

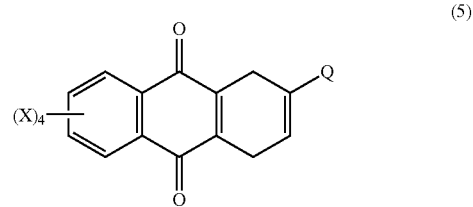
(5)

wherein in the formula (5): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom, and Q is a hydrogen atom, a $C_{1-15}$ alkyl group or a halogen atom,

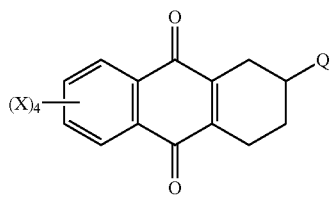

(6)

wherein in the formula (6): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; and Q is a hydrogen atom, a $C_{1-15}$ alkyl group or a halogen atom.

2. The radical polymerization control agent according to claim 1, wherein in the formula (4), X is a hydrogen atom, and Y and Z are a hydrogen atom.

3. The radical polymerization control agent according to claim 1, wherein in the formula (4), X is a hydrogen atom, Y is a hydroxy group, a $C_{1-15}$ alkyl group, a $C_{1-15}$ alkoxy group, an amino group or a halogen atom, and Z is a hydrogen atom.

4. The radical polymerization control agent according to claim 1, wherein in the formula (4), X is a hydrogen atom, Y is a hydroxy group or a methyl group, and Z is a hydrogen atom.

5. The radical polymerization control agent according to claim 1, wherein in the formula (4), X is a hydrogen atom, Y is a chlorine atom, and Z is a chlorine atom or an amino group.

6. A radical polymerizable composition, comprising
a radical polymerization control agent represented by formula (1), (2), or (3);
a radical polymerizable compound; and
a thermal radical polymerization initiator,

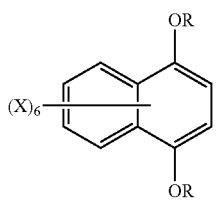

(1)

wherein in the formula (1): R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group, wherein a pair of adjacent Xs are optionally mutually bonded to form a saturated or unsaturated 6-membered ring, and the 6-membered ring formed by the pair of adjacent Xs is optionally further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

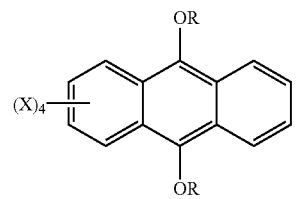

(2)

wherein in the formula (2): R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

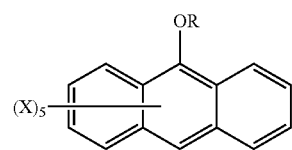

(3)

wherein in the formula (3): R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group.

7. The radical polymerizable composition according to claim 6, wherein the radical polymerizable compound is (meth)acrylic acid, a (meth)acrylic acid ester or styrene or an oligomer thereof.

8. A method for controlling radical polymerization, comprising:
applying a heat energy to a coating film formed by applying a radical polymerizable composition to a substrate, the radical polymerizable composition comprising a radical polymerization control agent represented by formula (1), (2), (3), (4), (5), or (6), a radical polymerizable compound, and a thermal radical polymerization initiator,
wherein the heat energy is applied while light within a wavelength range of from 300 nm to 500 nm is irradiated to the coating film in a state where a part of the coating film is shielded from the light such that radical polymerization of the radical polymerizable compound proceeds only in an unshielded portion of the coating film irradiated with the light,

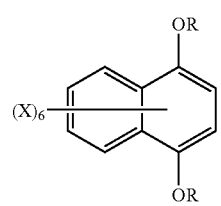

(1)

wherein in the formula (1): R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group, wherein a pair of adjacent Xs are optionally mutually bonded to form a saturated or unsaturated 6-membered ring, and the 6-membered ring formed by the pair of adjacent Xs is optionally further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

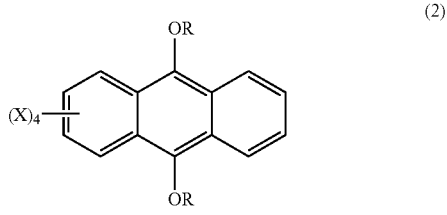

(2)

wherein in the formula (2): R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{7-13}$ substituted carbonyl group; and X is each independently a hydrogen atom, a $C_{1-15}$ alkyl group or a $C_{6-12}$ aryl group,

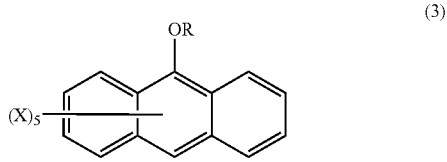

(3)

wherein in the formula (3): R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

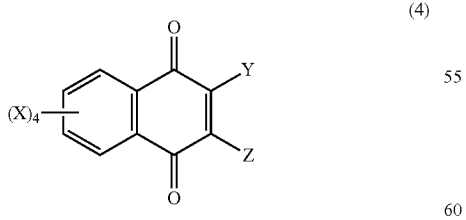

(4)

wherein in the formula (4): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; Y and Z are each independently a hydrogen atom, a hydroxy group, a $C_{1-15}$ alkyl group, a $C_{1-15}$ alkoxy group, an amino group or a halogen atom, wherein Y and Z are optionally mutually bonded to form a saturated or unsaturated 6-membered ring, and the 6-membered ring formed by Y and Z is optionally further substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

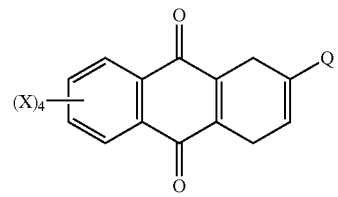

(5)

wherein in the formula (5): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; and Q is a hydrogen atom, a $C_{1-15}$ alkyl group or a halogen atom,

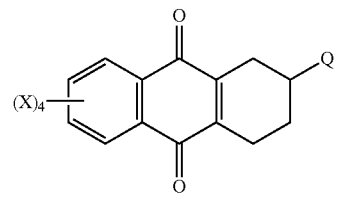

(6)

wherein in the formula (6): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; and Q is a hydrogen atom, a $C_{1-15}$ alkyl group or a halogen atom.

9. A method for controlling radical polymerization, comprising:
forming a film of a radical polymerizable composition comprising a radical polymerization control agent represented by formula (1), (2), (3), (4), (5), or (6), a radical polymerizable compound, and a thermal radical polymerization initiator; and
applying a heat energy to the film while irradiating a specific region of the film with light rays containing light within a wavelength range of from 300 nm to 500 nm such that radical polymerization of the radical polymerizable compound proceeds only in the specific region of the film,

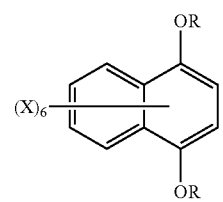

(1)

wherein in the formula (1): R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group, wherein a pair of adjacent Xs are optionally mutually bonded to form a saturated or unsaturated 6-membered ring, and the 6-membered ring formed by the pair of adjacent Xs is optionally further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

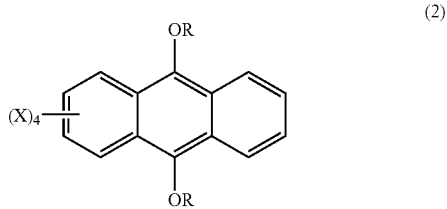

(2)

wherein in the formula (2): R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

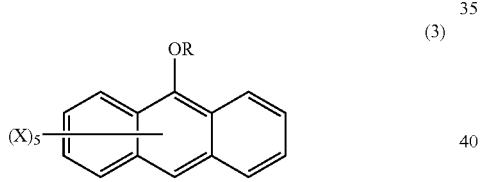

(3)

wherein in the formula (3): R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

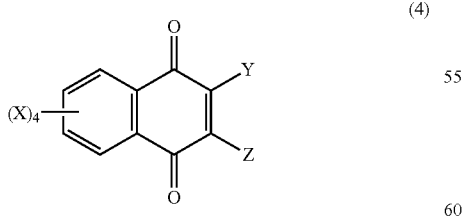

(4)

wherein in the formula (4): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; Y and Z are each independently a hydrogen atom, a hydroxy group, a $C_{1-15}$ alkyl group, a $C_{1-15}$ alkoxy group, an amino group or a halogen atom, wherein Y and Z are optionally mutually bonded to form a saturated or unsaturated 6-membered ring, and the 6-membered ring formed by Y and Z is optionally further substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

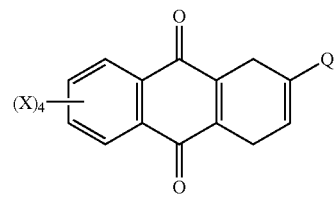

(5)

wherein in the formula (5): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; and Q is a hydrogen atom, a $C_{1-15}$ alkyl group or a halogen atom,

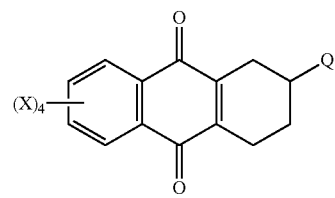

(6)

wherein in the formula (6): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; and Q is a hydrogen atom, a $C_{1-15}$ alkyl group or a halogen atom.

10. A method for controlling radical polymerization, comprising:

applying a radical polymerizable composition comprising a radical polymerizable compound, a radical polymerization control agent represented by formula (1), (2), (3), (4), (5), or (6), and a photoradical polymerization initiator, to a substrate, thereby forming a coating film of the radical polymerizable composition;

irradiating the coating film with light within a wavelength range of from 300 nm to 500 nm in a state where a part of the coating film is shielded from the light, and simultaneously applying a light energy capable of initiating polymerization of the radical polymerization compound to the coating film, such that radical polymerization of the radical polymerization compound proceeds only in an unshielded portion of the coating film irradiated with the light,

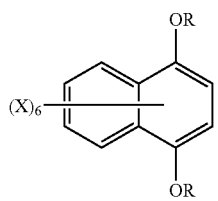

(1)

wherein in the formula (1): R is each independently a hydrogen atom, a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group, wherein a pair of adjacent Xs are optionally mutually bonded to form a saturated or unsaturated 6-membered ring, and the 6-membered ring formed by the pair of adjacent Xs is optionally further be substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

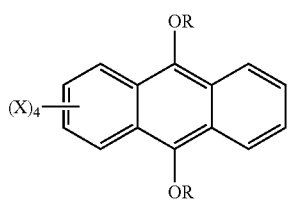

(2)

wherein in the formula (2): R is each independently a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

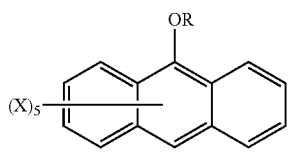

(3)

wherein in the formula (3): R is a $C_{1-15}$ alkyl group, a $C_{6-12}$ aryl group, a $C_{6-12}$ aralkyl group, a $C_{1-15}$ alkoxyalkyl group, a glycidyl group, a $C_{1-15}$ hydroxyalkyl group, a $C_{7-14}$ aryloxyalkyl group, a $C_{2-13}$ acyl group or a $C_{2-13}$ substituted carbonyl group; and X is each independently a hydrogen atom, a $C_{1-15}$ alkyl group or a $C_{6-12}$ aryl group,

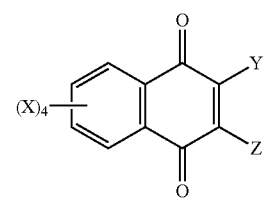

(4)

wherein in the formula (4): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; Y and Z are each independently a hydrogen atom, a hydroxy group, a $C_{1-15}$ alkyl group, a $C_{1-15}$ alkoxy group, an amino group or a halogen atom, wherein Y and Z are optionally mutually bonded to form a saturated or unsaturated 6-membered ring, and the 6-membered ring formed by Y and Z is optionally further substituted by a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom,

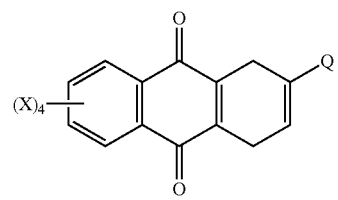

(5)

wherein in the formula (5): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; and Q is a hydrogen atom, a $C_{1-15}$ alkyl group or a halogen atom,

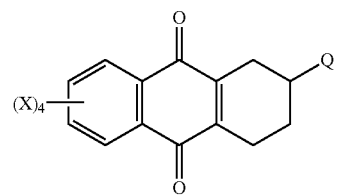

(6)

wherein in the formula (6): X is each independently a hydrogen atom, a $C_{1-15}$ alkyl group, a $C_{6-12}$ aryl group, a $C_{6-12}$ aralkyl group, a hydroxy group, a $C_{1-15}$ alkoxy group, a $C_{6-12}$ aryloxy group or a halogen atom; and Q is a hydrogen atom, a $C_{1-15}$ alkyl group or a halogen atom.

* * * * *